Figure 1:
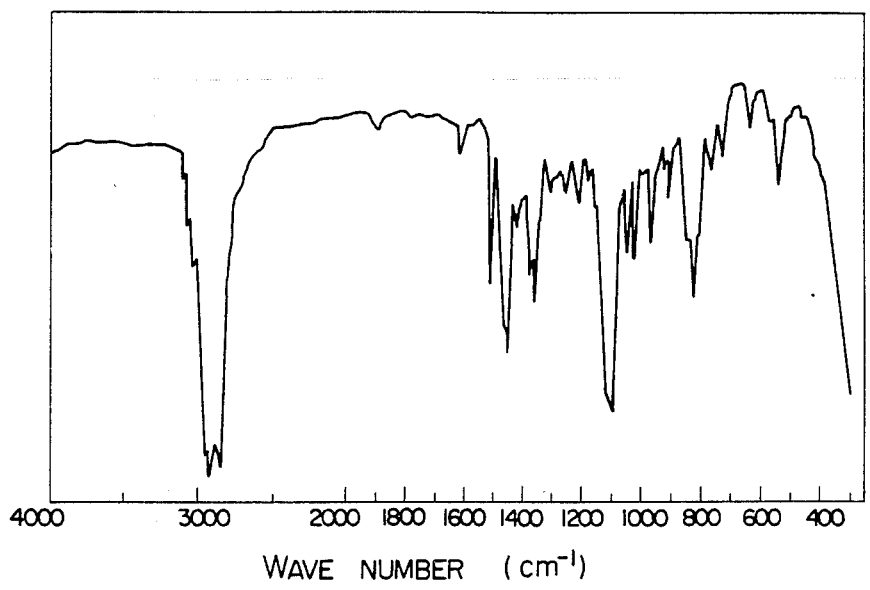

United States Patent [19]

Hirai et al.

[11] Patent Number: 4,564,694
[45] Date of Patent: Jan. 14, 1986

[54] COLORLESS LIQUID CRYSTALLINE COMPOUNDS

[75] Inventors: Yoichi Hirai; Tsunenori Fujii; Kaoru Koto; Kenji Suzuki, all of Soka; Masahiro Yoshida, Saitama; Hisashi Okawa, Kasukabe; Yoshiaki Okabe, Hitachi; Teruo Kitamura, Katsuta; Hisao Yokokura; Shintaroo Hattori, both of Hitachi; Akio Mukoh, Mito; Mikio Sato, Hitachi, all of Japan

[73] Assignees: Hitachi, Ltd.; Kanto Chemical Co., Inc., both of Tokyo, Japan

[21] Appl. No.: 352,019

[22] Filed: Feb. 24, 1982

[30] Foreign Application Priority Data

Feb. 25, 1981 [JP] Japan .................................. 56-25502
Jul. 10, 1981 [JP] Japan ................................ 56-107074
Nov. 18, 1981 [JP] Japan ................................ 56-183763
Nov. 18, 1981 [JP] Japan ................................ 56-183764

[51] Int. Cl.$^4$ .......................... C09K 3/34; G02F 1/13; C07C 69/74; C07C 69/76; C07C 41/00; C07C 41/02; C07C 41/18

[52] U.S. Cl. ...................................... 560/1; 544/242; 544/335; 544/315; 544/316; 544/318; 544/298; 549/372; 549/374; 252/299.5; 252/299.6; 252/299.61; 252/299.62; 252/299.63; 252/299.64; 252/299.65; 252/299.66; 252/299.67; 350/350 R; 350/350 S; 560/60; 560/73; 560/126; 568/659; 568/664; 568/665; 560/59; 560/72; 560/102; 560/108; 560/109; 560/118; 560/119

[58] Field of Search ............. 252/299.5, 299.6, 299.61, 252/299.62, 299.63, 299.64, 299.65, 299.66, 299.67; 350/350 R, 350 S; 568/607, 631, 659; 560/1, 126, 60, 73; 260/465 F, 465 D

[56] References Cited

U.S. PATENT DOCUMENTS

| 4,005,064 | 1/1977 | Dietrich et al. | 252/299.68 |
|---|---|---|---|
| 4,130,502 | 12/1978 | Eidenschink et al. | 252/299.63 |
| 4,158,011 | 6/1979 | Inukai et al. | 252/299.67 |
| 4,181,625 | 1/1980 | Eidenschink et al. | 252/299.63 |
| 4,198,130 | 4/1980 | Boller et al. | 252/299.5 |
| 4,229,315 | 10/1980 | Krause et al. | 252/299.63 |
| 4,261,652 | 4/1981 | Gray et al. | 252/299.62 |
| 4,279,770 | 7/1981 | Inukai et al. | 252/299.63 |
| 4,372,871 | 2/1983 | Toriyama et al. | 252/299.63 |
| 4,374,748 | 2/1983 | Inukai et al. | 252/299.66 |
| 4,431,564 | 2/1984 | Fukui et al. | 252/299.66 |
| 4,452,719 | 6/1984 | Inoue et al. | 252/299.63 |
| 4,468,040 | 8/1984 | Inoue et al. | 252/299.63 |

FOREIGN PATENT DOCUMENTS

| 3237020 | 5/1983 | Fed. Rep. of Germany | 252/299.63 |
|---|---|---|---|
| 105701 | 5/1974 | German Democratic Rep. | 252/299.63 |
| 52-68881 | 6/1977 | Japan | 252/299.68 |
| 57-77658 | 5/1982 | Japan | 252/299.67 |
| 57-99542 | 6/1982 | Japan | 252/299.63 |
| 57-10856 | 7/1982 | Japan | 252/299.66 |
| 58-49355 | 3/1983 | Japan | 252/299.63 |
| 58-121265 | 7/1983 | Japan | 252/299.63 |
| 58-121266 | 7/1983 | Japan | 252/299.63 |
| 58-131942 | 8/1983 | Japan | 252/299.63 |
| 58-134046 | 8/1983 | Japan | 252/299.63 |
| 58-134051 | 8/1983 | Japan | 252/299.62 |
| 58-134052 | 8/1983 | Japan | 252/299.63 |

OTHER PUBLICATIONS

Gray, G. W., Mol. Cryst. Liq. Cryst., vol. 63, pp. 3–18 (Jan. 1981).

*Primary Examiner*—Teddy S. Gron
*Attorney, Agent, or Firm*—Antonelli, Terry & Wands

[57] ABSTRACT

A colorless liquid crystalline compound having at least one 6-membered ring and non-cyclic end groups in the molecular skelton, said 6-membered containing two or more carbon atoms, at least one of which is directly bonded to a methylene group of a non-cyclic group having an alkoxy group at another end has a wide mesomorphic range. When said colorless liquid crystalline compound is mixed with a liquid crystal composition, the resulting mixture also has an enlarge mesomorphic range and in almost all cases has a reduced viscosity.

4 Claims, 17 Drawing Figures

WAVE NUMBER (cm⁻¹)

WAVE NUMBER (cm⁻¹)

WAVE NUMBER (cm⁻¹)

WAVE NUMBER (cm⁻¹)

WAVE NUMBER (cm⁻¹)

WAVE NUMBER (cm⁻¹)

WAVE NUMBER (cm⁻¹)

WAVE NUMBER (cm⁻¹)

WAVE NUMBER (cm⁻¹)

WAVE NUMBER (cm⁻¹)

WAVE NUMBER (cm$^{-1}$)

WAVE NUMBER (cm$^{-1}$)

WAVE NUMBER (cm⁻¹)

WAVE NUMBER (cm⁻¹)

WAVE NUMBER (cm$^{-1}$)

WAVE NUMBER (cm$^{-1}$)

COLORLESS LIQUID CRYSTALLINE COMPOUNDS

This invention relates to colorless liquid crystalline compounds.

In the present specification, the term "colorless liquid crystalline compounds" means liquid crystalline compounds which do not absorb visible light. The liquid crystalline compounds include not only liquid crystals but also compounds which are useful as constituents of liquid crystal compositions even if they themselves have no liquid crystal phase at room temperature.

In order to obtain a liquid crystal display element which is excellent in response properties not only at room temperature but also under the circumstances of low temperatures, it is necessary that the mesomorphic range should be extended to a low temperature range. This becomes possible if the reduction of the viscosity of liquid crystal compositions is realized.

Conventional representative liquid crystalline compounds:

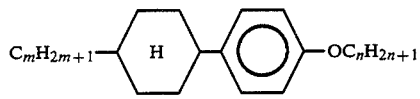

wherein m and n are individually an integer, are too highly viscous for the above-mentioned purpose. On the other hand, compounds of the similar general formula:

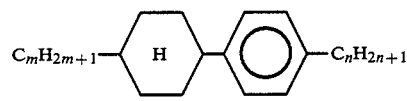

have a low viscosity but do not have a liquid crystal phase. From the difference between the compounds of each of the two formulas, the present inventors reached the following conclusion. In the case of compounds like the former compounds in which an oxygen atom is directly linked to

$\pi$ electrons of

and unshared electrons of the oxygen are conjugated and change places with each other, so that the dielectric constant becomes high, resulting in a high viscosity. On the other hand, the latter compounds have a low dielectric constant and hence have a low viscosity, however, since they have no polar atom or group such as an oxygen atom, the polarity of the whole molecule is small, so that they can have no liquid crystal phase. Accordingly, the present inventors have done further researches and accomplished this invention in the course of research on a molecular structure capable of giving properties which are intermediate between those of the former and latter compounds.

The compounds disclosed in Japanese Patent Appln Kokai (Laid-Open) No. 68,881/71 and represented by the general formula:

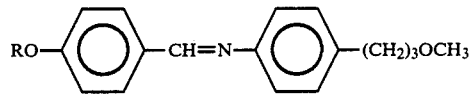

wherein R is $CH_3$, $C_2H_5$, n—$C_3H_7$ or n—$C_4H_9$, are liquid crystalline compounds having a low viscosity, and can extend the mesomorphic range. However these compounds are colored Schiff's base liquid crystalline compounds.

Objects of this invention are to provide colorless liquid crystalline compounds and colorless liquid crystal compositions capable of extending the mesomorphic range to a low temperature range, and provide liquid crystal display elements excellent in response properties by mainly utilizing such a property of the colorless liquid crystal compositions.

The colorless liquid crystalline compounds of this invention are characterized by having in their molecular skeletons at least one 6-membered ring, said at least one 6-membered ring containing two or more carbon atoms, a methylene group being directly linked to at least one of said carbon atoms, said methylene group constituting one end of a non-cyclic group, and the other end group of said non-cyclic group being an alkoxy group.

Herein, the 6-membered ring includes those contained in fused ring organic groups as in the case of

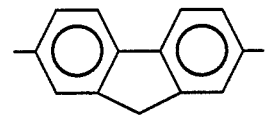

not to mention single ring organic groups such as

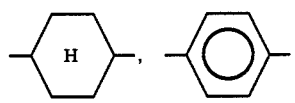

and the like. The reason why at least one ring contained in the molecular skeleton is a 6-membered ring is that first, said ring should be an even-number-membered ring because the molecule of liquid crystalline compound should be linear; and secondly, when said ring is a 8-membered ring, the resulting compound is very unstable and cannot be utilized as liquid crystalline compounds. For requiring the molecules of liquid crystalline compounds to be linear, it is desirable that the position of bonding of the aforesaid non-cyclic group to the 6-membered ring is para to another substituent bonded to said 6-membered ring.

As the aforesaid non-cyclic group, the following groups are preferable: —$(CH_2O)_nC_mH_{2m+1}$, —$(CH_2)_nOC_mH_{2m+1}$, —$(CH_2)_nO(CH_2)_lOC_mH_{2m+1}$ and —$CH_2O(CH_2)_nOC_mH_{2m+1}$ (wherein all of l, m and n are individually an integer). In each of the formulas, each of n and l particularly preferably has a value of 1 to 8 for the two reasons that (1) the closer the oxygen atom comes to the 6-membered ring, the more polar the molecular becomes and (2) the smaller the number of the atoms other than carbon atoms and hydrogen atoms, such as oxygen atoms, the lower the viscosity becomes. In the case of a nematic liquid crystal, m particularly preferably has a value of 1 to 12.

Colorless liquid crystalline compounds satisfying these optimum conditions are represented by compounds of the general formula

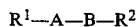  (I)

or

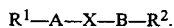  (II)

In both the general formulas (I) and (II), $R^1$ is a non-cyclic group represented by $-(CH_2O)_nC_mH_{2m+1}$, $-(CH_2)_nOC_mH_{2m+1}$, $-(CH_2)_nO(CH_2)_lOC_mH_{2m+1}$, or $-CH_2O(CH_2)_nOC_mH_{2m+1}$ (wherein n and l are individually an integer of 1 to 8 and m is an integer of 1 to 12, and hereinafter the same applies), and $R^2$ is an alkyl group, an alkoxy group, an acyl group, an acyloxy group, an alkoxycarbonyl group, a cyano group, a nitro group, a halogen group, a fluoroalkyl group, a fluoroalkoxy group or a non-cyclic group represented by $-O(CH_2)_nOC_mH_{2m+1}$, $-(CH_2O)_nC_mH_{2m+1}$, $-(CH_2)_nOC_mH_{2m+1}$, $-(CH_2)_nO(CH_2)_lOC_mH_{2m+1}$ or $-CH_2O(CH_2)_nOC_mH_{2m+1}$. In both the general formulas (I) and (II), both A and B are individually a group at least having one or more 6-membered ring which is represented by

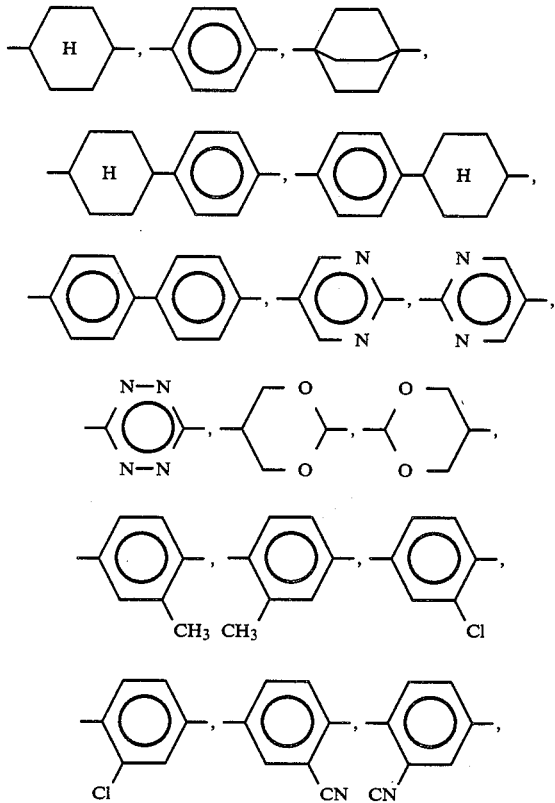

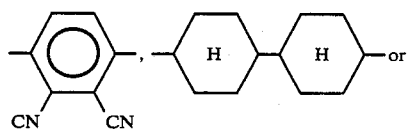

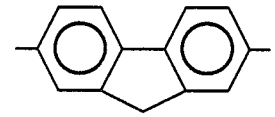

Further, X in the general formula (II) is a group represented by $-COO-$, $-OCO-$, $-CH=CH-$, $-C\equiv C-$, $-CH_2-CH_2-$ or $-CH_2O-$.

Colored azo, azoxy or the like liquid crystalline compounds, to say nothing of colored Shiff's base liquid crystalline compounds such as the above-mentioned conventional examples, are not the object of this invention.

In the attached drawings, all of FIGS. 1 to 17 are infrared absorption spectra of various colorless liquid crystalline compounds of this invention.

This invention is further explained below in detail referring to Examples. In the following explanation, $R^4$ and $R^5$ in the general formulas mentioned below individually represent an alkyl group preferably having 1 to 12 carbon atoms. $R^4$ and $R^5$ may have the same number of or different numbers of carbon atoms and may be straight-chain or branched group. The values of the phase transition temperatures and the melting points change a little depending upon the purities of the compounds. The letter S denotes a smectic phase, the letter N a nematic phase and the letter I an isotropic phase. For example, the crystal-to-nematic transition is symbolized by (C-N) transition, and the nematic-to-isotropic transition by (N-I) transition. The unit of the phase transition temperatures is °C. In explanation of the phase transition temperatures, the numerical values in the parentheses indicate the transition temperatures of the monotropic transition in which phase transition does not take place in the course of heating and it takes place to show a liquid crystal phase only in the course of cooling.

EXAMPLE 1

(Process for producing a colorless liquid crystalline compound represented by the general formula:

and its physical properties)
In a flask were placed 31.2 g of lithium aluminum hydride (Li[AlH₄]) and 200 ml of tetrahydrofuran

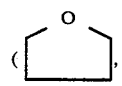

hereinafter referred to as THF) to obtain a suspension. One liter of a solution of 180 g of

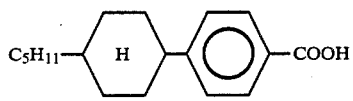

in THF was added dropwise to the suspension with stirring under ice-cooling, and after completion of the addition, the resulting solution was further stirred at room temperature continuously for 2 hours. Subsequently, the reaction solution was poured into 3 liters of dilute hydrochloric acid, and the thus obtained mixture was stirred, after which the organic layer was separated, and the solvent was distilled off to obtain

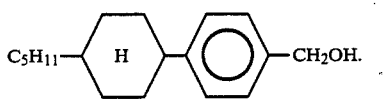

In 40 g of thionyl chloride ($SOCl_2$) was dissolved 39 g of

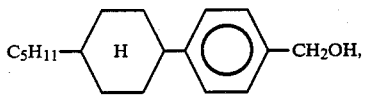

and the resulting solution was refluxed for 4 hours, after which the reaction solution was poured into 500 ml of ice water, and then extracted with benzene

The benzene was distilled off to obtain

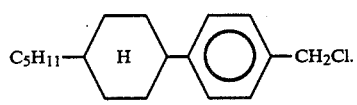

In another flask was placed 100 ml of n-propyl alcohol ($C_3H_7OH$), and 0.4 g of metallic sodium (Na) was added thereto, after which the thus obtained mixture was heated to completely dissolved the latter in the former. To the resulting solution was added 5 g of

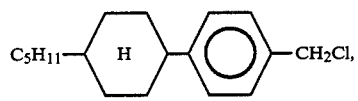

and the resulting solution was heated and refluxed for 4 hours. This reaction solution was poured into 300 ml of water and the thus obtained mixture was extracted with diethyl ether (($C_2H_5)_2O$), after which the ($C_2H_5)_2O$ was distilled off and the residue was recrystallized to obtain a colorless liquid crystalline compound:

(Sample 1)

The values of elementary analysis (C 83.4%, H 11.30%) of the sample 1 were in good agreement with the values calculated from the molecular weight (C 83.38%, H 11.30%) for $C_{21}H_{34}O$. In addition, the infrared absorption spectrum of the sample 1 was as shown in FIG. 1, and an absorption due to the ether linkage appeared at 1100 $cm^{-1}$. From the relation between these two facts and the starting compounds, the sample 1 was identified as the liquid crystalline compound of the above formula.

There are shown in Table 1 the phase transition temperatures of the sample 1 and other samples obtained by a production process according to that of the sample 1.

TABLE 1

| Sample | $R^4$ | $R^5$ | C-I | N-I |
|---|---|---|---|---|
| 1 | $C_5H_{11}$ | $C_3H_7$ | 2.5 | (−38) |
| 2 | $C_5H_{11}$ | $C_5H_{11}$ | 3 | (−42) |
| 3 | $C_5H_{11}$ | $C_8H_{17}$ | 16 | (−30) |
| 4 | $C_5H_{11}$ | $C_2H_5$ | 19 | (−40) |
| 5 | $C_5H_{11}$ | $CH_3$ | 9.5 | (−10) |
| 6 | $C_7H_{15}$ | $CH_3$ | 18 | (7.0) |
| 7 | $C_7H_{15}$ | $C_2H_5$ | 9.5 | (−10) |
| 8 | $C_7H_{15}$ | $C_3H_7$ | 5 | (−18) |
| 9 | $C_7H_{15}$ | $C_4H_9$ | 2 | (−21) |
| 10 | $C_3H_7$ | $C_8H_{17}$ | 12 | (−45) |
| 11 | $C_3H_7$ | $C_6H_{13}$ | 1 | (−30) |
| 12 | $C_3H_7$ | $C_4H_9$ | −10 | (−27) |
| 13 | $C_3H_7$ | $C_3H_7$ | −4 | (−47) |
| 14 | $C_3H_7$ | $CH_3$ | 7.5 | (−21) |
| 15 | $C_2H_5$ | $C_3H_7$ | −10 | (−37) |
| 16 | $CH_3$ | $C_3H_7$ | −19 | (−40) |

EXAMPLE 2

(Process for producing a colorless liquid crystalline compound represented by the general formula:

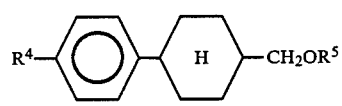

and its physical properties)

In a flask were placed 31.2 g of Li[$AlH_4$] and 200 mg of THF to obtain a suspension. A solution of 180 g of

in 1 liter of THF was added dropwise to the suspension with stirring under ice-cooling, and after completion of the addition, the resulting solution was further stirred at room temperature continuously for 6 hours. Subsequently, the reaction solution was poured into dilute hydrochloric acid, and the thus obtained mixture was stirred, after which the organic layer was separated, and the solvent was distilled off to obtain

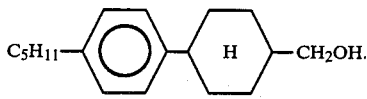

In another flask were placed 35.7 g of SOCl$_2$, 1.4 g of pyridine

and 100 ml of benzene, and the resulting mixture was refluxed and stirred. To the mixture was added 39 g of

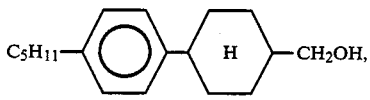

and the thus obtained solution was refluxed and stirred for 4 hours. This reaction solution was poured into water, and then extracted with benzene, after which the benzene was distilled off to obtain

In further another flask was placed 100 ml of C$_3$H$_7$OH and 0.4 g of Na was added thereto, after which the resulting mixture was heated to reflux temperature. To the solution was added 5 g of the

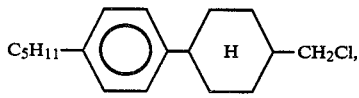

and the resulting solution was refluxed for 3 to 4 hours. This reaction solution was concentrated, poured into water, and then extracted with (C$_2$H$_5$)$_2$O, after which the (C$_2$H$_5$)$_2$O was distilled off and the residue was recrystallized to obtain a colorless liquid crystalline compound:

(Sample 17)

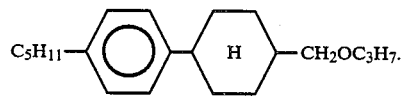

Figure 2:
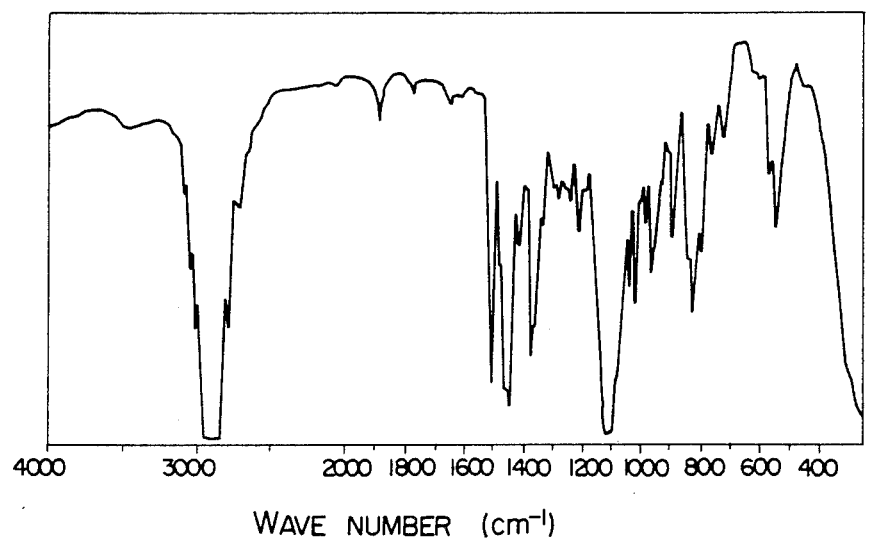

The values of elementary analysis (C 83.30%, H 11.42%) of the sample 17 were in good agreement with the values calculated from the molecular weight for C$_{21}$H$_{34}$O. In addition, the infrared absorption spectrum of the sample 17 was as shown in FIG. 2, and an absorption due to the ether linkage appeared at 1110 cm$^{-1}$. From the relation between these two facts and the starting compounds, the sample 17 was identified as the liquid crystalline compound of the above formula.

There are shown the phase transition temperatures of the sample 17 and other samples obtained by a production process according to that of the sample 17.

TABLE 2

| Sample | R$^4$ | R$^5$ | C-I | N-I |
|---|---|---|---|---|
| 17 | C$_5$H$_{11}$ | C$_3$H$_7$ | 3 | (−53) |
| 18 | C$_5$H$_{11}$ | C$_4$H$_9$ | −11 | (−39) |
| 19 | C$_5$H$_{11}$ | C$_5$H$_{11}$ | 5 | (−21) |
| 20 | C$_5$H$_{11}$ | C$_2$H$_5$ | −8 | (−44) |
| 21 | C$_5$H$_{11}$ | CH$_3$ | 0 | (−17) |
| 22 | C$_3$H$_7$ | C$_5$H$_{11}$ | −13 | (−42) |
| 23 | C$_3$H$_7$ | C$_3$H$_7$ | −19 | (−40) |
| 24 | C$_3$H$_7$ | C$_2$H$_5$ | −1 | (−43) |
| 25 | C$_2$H$_5$ | C$_5$H$_{11}$ | −7 | (−70) |
| 26 | C$_2$H$_5$ | C$_3$H$_7$ | −16 | (−70) |

EXAMPLE 3

(Process for producing a colorless liquid crystalline compound represented by the general formula:

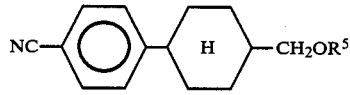

and its physical properties)

In a flask were placed 158 g of

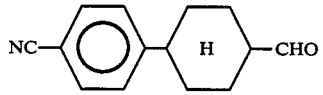

and 600 ml of C$_2$H$_5$OH, and the resulting mixture was stirred under ice-cooling. Thereafter, 17.1 g of sodium boron hydride (Na[BH$_4$]) was gradually added, and the thus obtained mixture was stirred at room temperature for 2 hours. Subsequently, the reaction solution was poured into water, and then extracted with (C$_2$H$_5$)$_2$O, and the (C$_2$H$_5$)$_2$O was distilled off to obtain

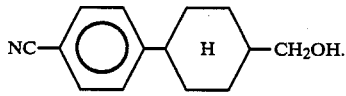

Next, 35.7 g of SOCl$_2$ was placed in another flask and refluxed and stirred, and 32 g of the

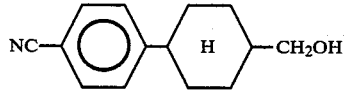

was added thereto, after which the resulting solution was refluxed and stirred for 4 hours. This reaction solution was poured into water, and the organic layer was separated and the benzene was distilled off to obtain

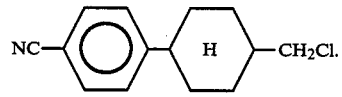

In further another flask were placed 100 ml of $C_3H_7OH$ and 0.4 g of Na, and the resulting mixture was heated to reflux temperature, after which 4.2 g of the above

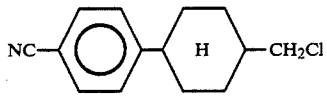

was added thereto, and the thus obtained solution was stirred for 3 to 4 hours. This reaction solution was poured into water and extracted with $(C_2H_5)_2O$ and the $(C_2H_5)$ was distilled off. The residue was recrystallized to obtain a colorless liquid crystalline compound:

(Sample 27)

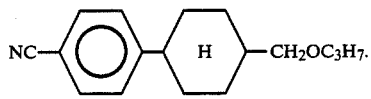

Figure 3:
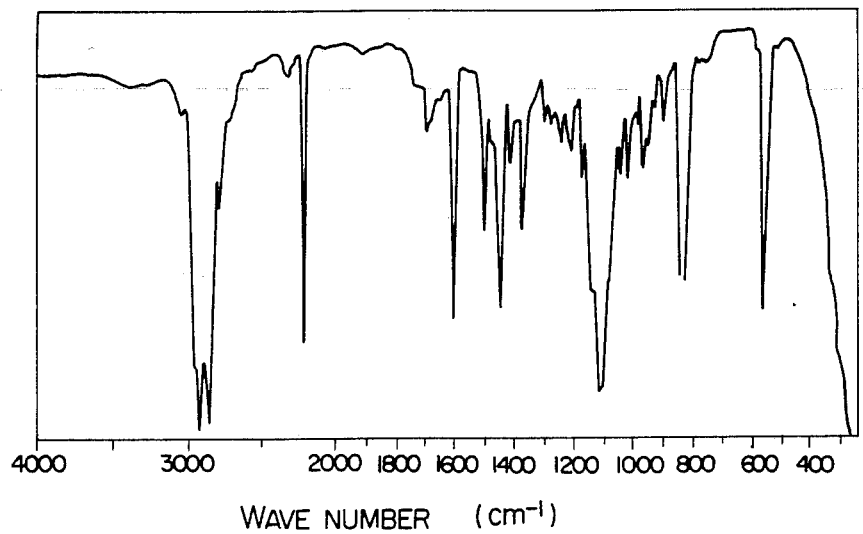

The values of elementary analysis (C 79.13%, H 8.89%, N 5.31%) of the sample 27 were in good agreement with the values calculated from the molecular weight (C 79.33%, H 9.01%, N 5.44%) for $C_{17}H_{23}NO$. In addition, the infrared absorption spectrum of the sample 27 was as shown in FIG. 3, and an absorption band of the cyano group appeared at 2220 cm$^{-1}$ and that of the ether linkage at 1115 cm$^{-1}$. From the relation between these two facts and the starting compounds, the sample 27 was identified as the liquid crystalline compound of the above formula.

The sample 27 was a monotropic crystal having phase transition temperatures of 21° C. for (C-I) transition and −70° C. for (N-I) transition.

EXAMPLE 4

(Process for producing a colorless liquid crystalline compound represented by the general formula:

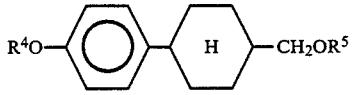

and its physical properties)

In a flask was placed 1 liter of $C_2H_5OH$, after which 10 g of sodium hydroxide (NaOH) and 44 g of

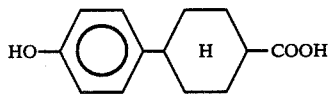

were added, and the resulting mixture was heated and refluxed for 2 hours to completely dissolve them in the $C_2H_5OH$. Subsequently, 40 g of n-butyl iodide ($C_4H_9I$) was added to the resulting solution, and the thus obtained mixture was refluxed with stirring for 6 hours. Thereafter, the ethyl alcohol ($C_2H_5OH$) was distilled off under reduced pressure, and the residue was dissolved in water, after which hydrochloric acid was added thereto, and the deposited crystal was washed with water to obtain

Next, 3.2 g of Li[AlH$_4$] was suspended in 50 ml of THF in another flask, and a solution of 19 g of the

in 100 ml of THF was added thereto dropwise under ice-cooling. The resulting mixture was stirred for 2 hours and them poured into 200 ml of dilute hydrochloric acid, after which the thus obtained mixture was vigorously stirred, and then extracted with benzene. The benzene was distilled off to obtain

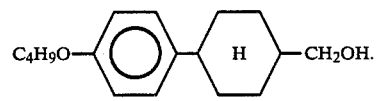

In further another flask was placed 12 g of the

and 30 g of $SOCl_2$ was added to dissolve it, after which the resulting solution was heated and refluxed for 4 hours. The reaction solution was poured into ice water and extracted with benzene. And then the benzene was distilled off to obtain

In still another flask was placed 50 ml of $C_3H_7OH$ and 0.4 of Na, and the resulting mixture was heated to reflux temperature, after which 5.2 g of the above

was added and the thus obtained solution was heated and refluxed for 4 hours. Thereafter, this reaction solution was concentrated, and ice water was added thereto, after which the resulting mixture was extracted with $(C_2H_5)_2O$ and the $C(C_2H_5)_2O$ was distilled off. The residue was recrystallized to obtain a colorless liquid crystalline compound:

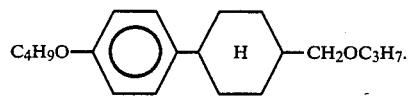 (Sample 28)

Figure 4:
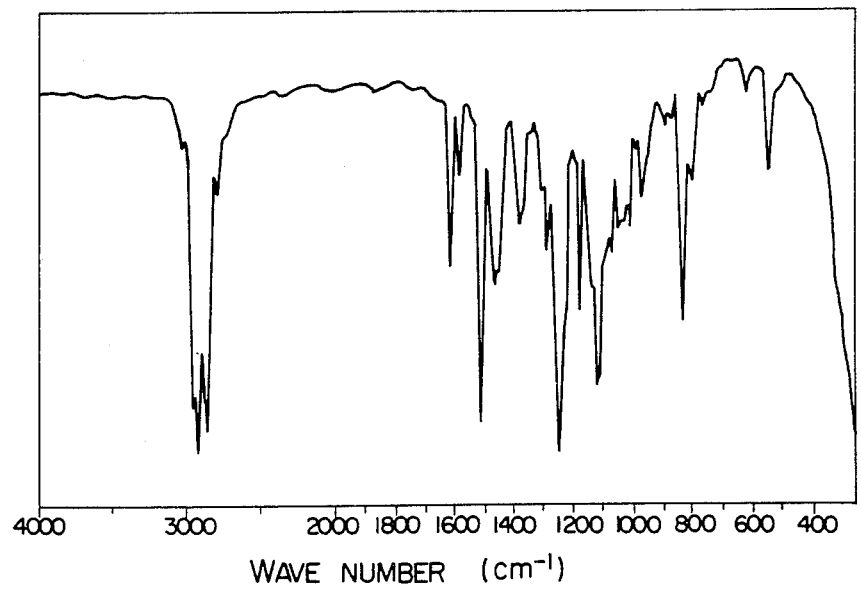

The values of elementary analysis (C 78.80%, H 11.07%) of the sample 28 were in good agreement with the valves calculated from the molecular weight (C 78.90%, H 10.59%) for $C_{20}H_{32}O_2$. In addition, the infrared absorption spectrum of the sample 28 was as shown in FIG. 4, and an absorption band of the phenoxy ether appeared at 1250 cm$^{-1}$ and that of the ether linkage at 1120 cm$^{-1}$. From the relation between these two facts and the starting compounds, the sample was identified as the liquid crystalline compound of the above formula.

The sample 28 was a monotropic smectic liquid crystal having phase transition temperatures of $-8°$ C. for (C-I) transistion and $-50°$ C. for (I-S) transition.

EXAMPLE 5

(Process for producing a colorless liquid crystalline compound represented by the general formula:

and its physical properties)

In a flask were placed 62.4 g of Li[AlH$_4$] and 200 ml of THF and vigorously stirred to obtain a suspention. After the suspention was cooled with ice, a solution of 161 g of

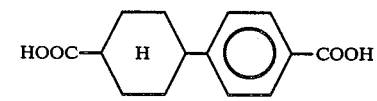

in 1 liter of THF was added dropwise. Thereafter, the resulting solution was stirred at room temperature for 4 hours, and further poured into 2 liters of dilute hydrochloric acid, after which the resulting mixture was stirred and then extracted with benzene. And then the benzene was distilled off to obtain

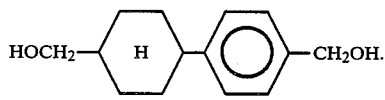

A solution consisting of 71.4 g of SOCl$_2$, 100 ml of benzene and 2.8 g of pyridine was prepared in another flask, and 33 g of the

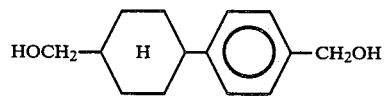

was added thereto, after which the resulting solution was heated and refluxed. After 4 hours, this reaction solution was poured into ice water and extracted with benzene. And then the benzene was distilled off to obtain

In further another flask were placed 200 ml of $C_3H_7OH$ and 0.8 g of Na, and the Na was dissolved in the $C_3H_7OH$ by heating, after which 4.6 g of the above

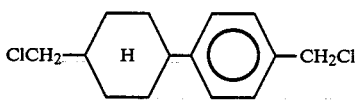

was added thereto, and the resulting solution was heated and refluxed for 4 hours. This reaction solution was poured into water, and extracted with $(C_2H_5)_2O$ and the $(C_2H_5)_2O$ was distilled off. The residue was recrystallized to obtain a colorless liquid crystalline compound:

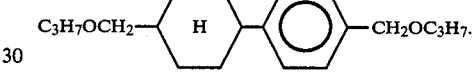 (Sample 29)

Figure 5:
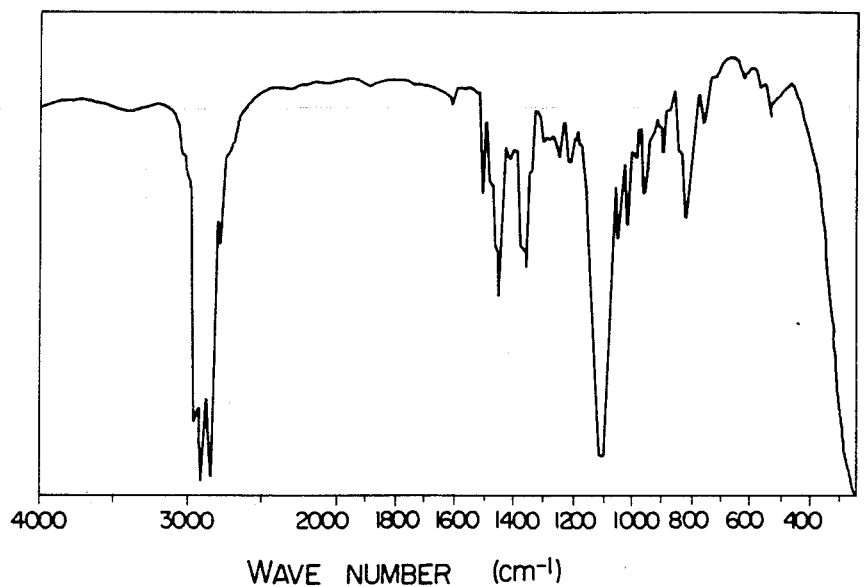

The values of elementary analysis (C 78.09%, H 10.65%) of the sample 29 were in good agreement with the values calculated from the molecular weight (C 78.90%, H 10.59%) for $C_{20}H_{32}O_2$. In addition, the infrared absorption spectrum of the sampel 29 was as shown in FIG. 5, and an absorption band of the ether linkage appeared at 1100 cm$^{-1}$. From the relation between these two facts and the starting compounds, the sample 29 was identified as the liquid crystalline compound of the above formula.

The sample 29 was a monotropic liquid crystal having a phase transition temperature of $-44°$ C. for (I-N) transition.

EXAMPLE 6

(Process for producing a colorless liquid crystalline compound represented by the general formula:

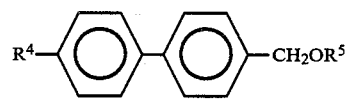

and its physical properties)

In a flask were placed 189 g of

and 600 ml of $C_2H_5OH$, and cooled with ice and stirred. Thereto was gradually added 17.1 g of Na[BH$_4$], after which the resulting mixture was stirred at room temperature continuously for 2 hours. Thereafter, 10 ml of acetic acid (CH$_3$COOH) was added, followed by adding thereto 2 liters of water, and the thus obtained mixture was extracted with $(C_2H_5)_2O$, and then the $(C_2H_5)_2O$ was distilled off to obtain

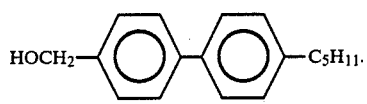

Next, a solution consisting of 35.7 g of $SOCl_2$, 1.4 g of pyridine and 100 ml of benzene was prepared in another flask, and 38 g of the

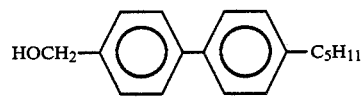

was added thereto, after which the resulting solution was heated and refluxed for 4 hours. This reaction solution was poured into water and extracted with benzene. And then the benzene was distilled off to obtain

In further another flask, 0.4 g of Na was dissolved in 100 ml of $C_3H_7OH$, and 4.9 g of the

was added thereto, after which the resulting solution was heated and stirred for 4 hours. This reaction solution was poured into water and extracted with $(C_2H_5)_2O$, and then the residue obtained by distilling off the $(C_2H_5)_2O$ was recrystallized to obtain a colorless liquid crystalline compound:

(Sample 30)

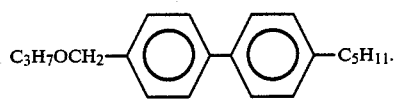

Figure 6:
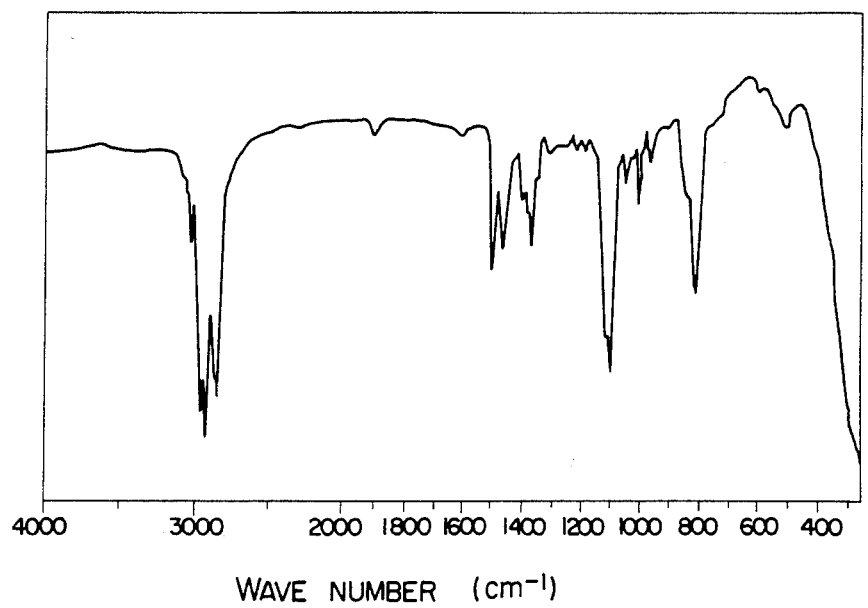

The values of elementary analysis (C 84.83%, H 9.73%) of the sample 30 were in good agreement with the values calculated from the molecular weight (C 85.08%, H 9.52%) for $C_{21}H_{28}O$. In addition, the infrared absorption spectrum of the sample 30 was as shown in FIG. 6, and an absorption band of the ether linkage appeared at 1100 cm$^{-1}$. From the relation between these two facts and the starting compounds, the sample 30 was identified as the liquid crystalline compound of the above formula.

There are shown in Table 3 the phase transition temperatures of the sample 30 and other samples obtained by a production process according to that of the sample 30.

TABLE 3

| Sample | R$^4$ | R$^5$ | C-I | S-I |
|---|---|---|---|---|
| 30 | C$_5$H$_{11}$ | C$_3$H$_7$ | 27 | (21) |

TABLE 3-continued

| Sample | R$^4$ | R$^5$ | C-I | S-I |
|---|---|---|---|---|
| 31 | C$_5$H$_{11}$ | C$_5$H$_{11}$ | 16 | (10) |
| 32 | C$_5$H$_{11}$ | CH$_3$ | 48 | (47) |

EXAMPLE 7

(Process for producing a colorless liquid crystalline compound represented by the general formula:

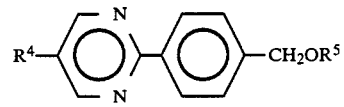

and its physical properties,

A solution of 190 g of

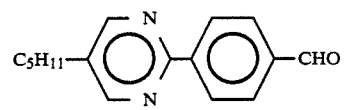

in 600 ml of $C_2H_5OH$ was prepared in a flask, and 17.1 g of Na[BH$_4$] was gradually added with stirring under ice-cooling. Thereafter, the resulting mixture was stirred continuously for 3 hours, after which 15 ml of acetic acid and 2 liters of water were added thereto, and the thus obtained mixture was extracted with $(C_2H_5)_2O$, and then the $(C_2H_5)_2O$ was distilled off to obtain

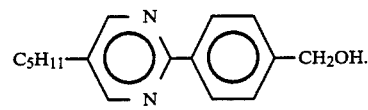

Next, a solution consisting of 35.7 g of $SOCl_2$, 1.4 g of pyridine and 100 ml of benzene was prepared in another flask, and 38 g of the

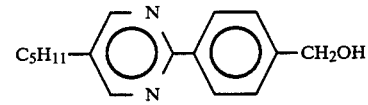

was added thereto, after which the resulting solution was heated and stirred for 5 hours. This reaction solution was poured into water and extracted with benzene. And then the benzene was distilled off to obtain

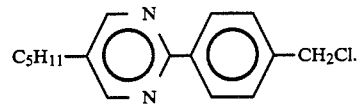

In further another flask, 0.4 g of Na was dissolved in 100 ml of $C_3H_7OH$, and 4.9 g of the

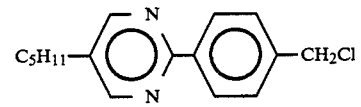

was added thereto, after which the resulting mixture was heated and refluxed. After 4 hours, this reaction solution was allowed to cool, poured into water, and then extracted with $(C_2H_5)_2O$. Then the residue obtained by distilling off the $(C_2H_5)_2O$ was recrystallied to obtain a colorless liquid crystalline compound:

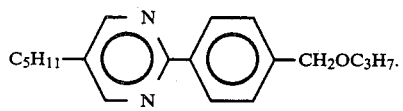
(Sample 33)

Figure 7:
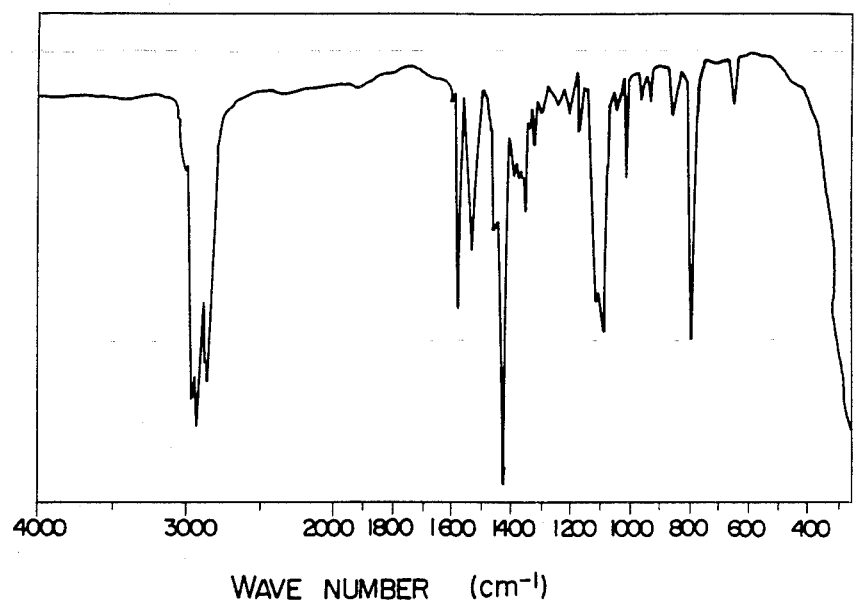

The values of elementary analysis (C 76.05%, H 8.85%, N 9.45%) of the sample 33 were in good agreement with the values calculated from the molecular weight (C 76.47%, H 8.78%, N 9.38%) for $C_{19}H_{26}N_2O$. In addition, the infrared absorption spectrum of the sample 33 was as shown in FIG. 7, and an absorption band of the ether linkage appeared at 1100 cm$^{-1}$. From the relation between these two facts and the starting compounds, the sample 33 was identified as the liquid crystalline compound of the above formula.

The phase transition temperature of the sample 33 was 21° C. for (C-I) transistion. The phase transition temperature of

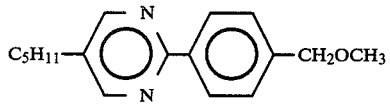
(Sample 34)

produced by a production process according to that of the sample 33 was 51° C. for (C-I) transition.

EXAMPLE 8

(Process for producing a colorless liquid crystalline compound represented by the general formula:

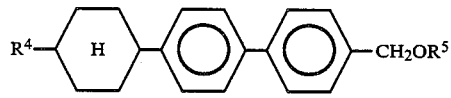

and its physical properties)

A solution of 67 g of

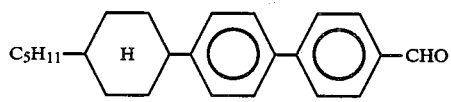

in 500 ml of $C_2H_5OH$ was prepared in a flask, and 11.4 g of $Na[BH_4]$ was gradually added with stirring under ice-cooling. Thereafter, the resulting mixture was stirred continuously for 3 hours, after which 30 ml of $CH_3COOH$ was added thereto, and the thus obtained mixture was poured into water and extracted with $(C_2H_5)_2O$, and then the $(C_2H_5)_2O$ was distilled off to obtain

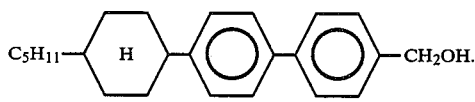

Next, 30 g of the

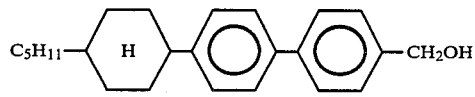

was added to 150 ml of $SOCl_2$, and the resulting solution was refluxed for 6 hours and then poured into ice water. Subsequently, the precipitate was collected by filtration and washed with water to obtain

In further another flask, 0.4 g of Na was dissolved in 30 ml of $C_3H_7OH$, and a solution of 30 g of the

in 150 ml of N,N-dimethylformamide $((CH_3)_2NCHO)$ was added thereto, after which the resulting solution was heated and stirred for 5 hours. Thereafter, this reaction solution was poured into water, and the precipitate was collected by filtration and recrystallized to obtain a colorless liquid crystalline compound:

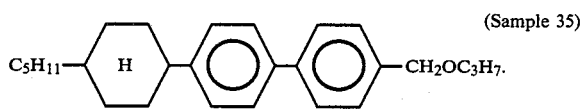
(Sample 35)

Figure 8:
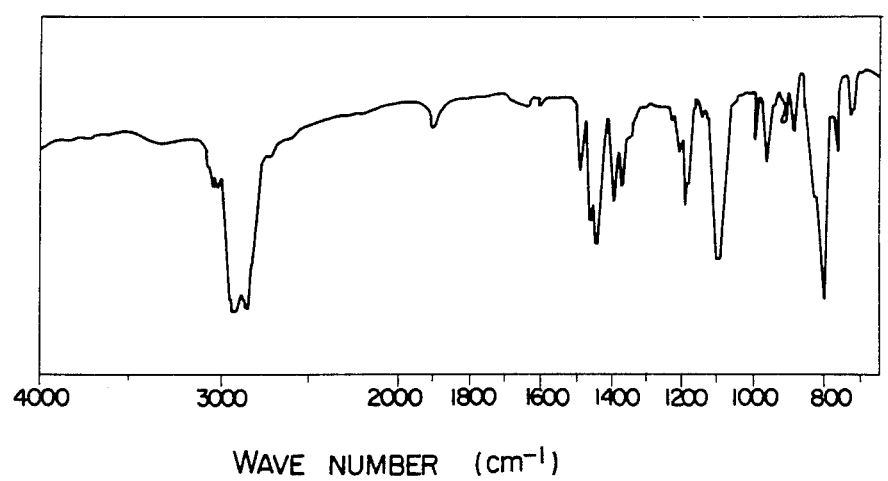

The values of elementary analysis (C 85.19%, H 10.23%) of the sample 35 were in good agreement with the values calculated from the molecular weight (C 85.66%, H 10.12%) for $C_{27}H_{38}O$. In addition, the infrared absorption spectrum of the sample 35 was as shown in FIG. 8, and an absorption band of the ether linkage appeared at 1100 cm$^{-1}$. From the relation between these two facts and the starting compounds, the sample 35 was identified as the liquid crystalline compound of the above formula.

The phase transition temperatures of the sample 35 were 152° C. for (C-N) transition and 175° C. for (N-I) transition. The phase transition temperatures of

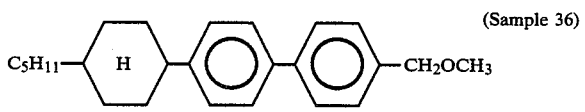
(Sample 36)

produced by a production process according to that of the sample 35 were 158° C. for (C-N) transition and 177° C. for (N-I) transition.

EXAMPLE 9

(Process for producing a colorless liquid crystalline compound represented by the general formula:

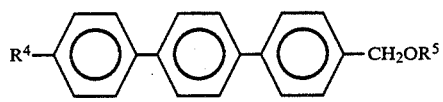

and its physical properties)
By use of

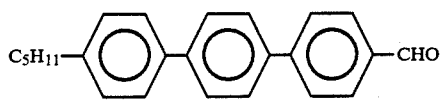

as a starting material, (Sample 37)

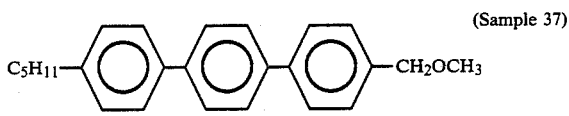

was obtained by a production process according to that of the sample 35.

Figure 9:
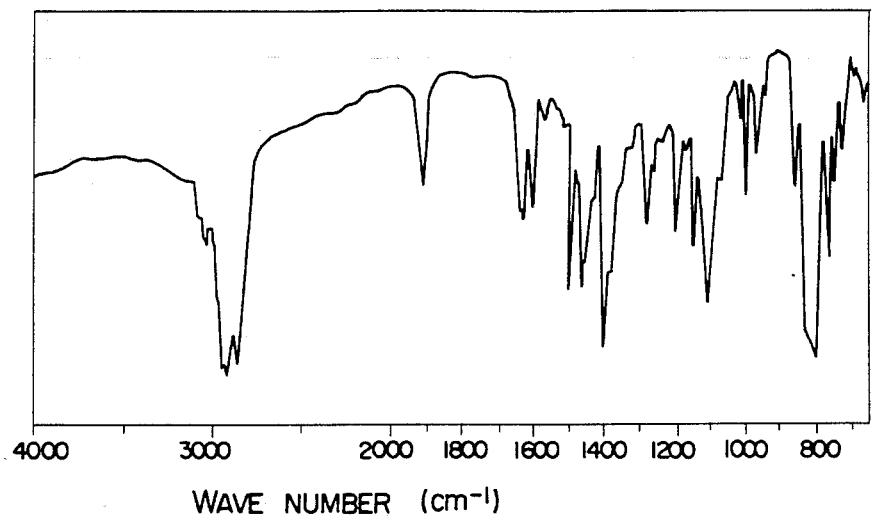

The values of elementary analysis (C 87.25%, H 8.43%) of the sample 37 were in good agreement with the values calculated from the molecular weight (C 87.16%, H 8.19%) for $C_{25}H_{28}O$. In addition, the infrared absorption spectrum of the sample 37 was as shown in FIG. 9, and an absorption band of the ether linkage appeared at 1100 cm$^{-1}$. From the relation between these two facts and the starting compounds, the sample 37 was identified as the liquid crystalline compound of the above formula.

The phase transition temperatures of the sample 37 were 233° C. for (C-S) transition, 240° C. for (S-N) transition, and 245° C. for (N-I) transition.

EXAMPLE 10

(Process for producing a colorless liquid crystalline compound represented by the general formula:

and its physical properties)

In a flask were placed 50 ml of $CH_3O(CH_2)_2OH$ and 0.4 g of Na, and the latter was dissolved in the former. Thereto was added 5 g of the intermediate

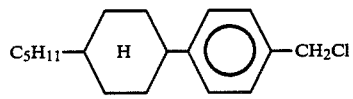

produced in Example 1, and the resulting solution was stirred at 80° C. for 4 hours. Thereafter, the reaction solution was poured into water and extracted with $(C_2H_5)_2O$ and then $(C_2H_5)_2O$ was distilled off and the residue was recrystallized to obtain a colorless liquid crystalline compound:

(Sample 38)

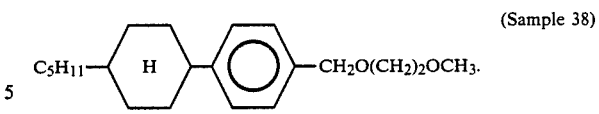

The values of elementary analysis (C 79.31%, H 10.62%) of the sample 38 were in good agreement with the values calculated from the molecular weight (C 79.19%, H 10.76%) for $C_{21}H_{34}O_2$. In addition, the infrared absorption spectrum of said compound almost agreed with that shown in FIG. 1. From the relation between these two facts and the starting compounds, the sample 38 was identified as the liquid crystalline compound of the above formula.

The phase transition temperature of the sample 38 was 95° C. for (C-I) transition.

EXAMPLE 11

(Process for producing a colorless liquid crystalline compound represented by the general formula:

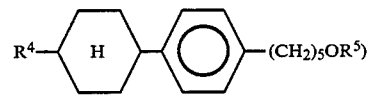

In a flask were placed 300 ml of anhydrous methylene dichloride ($CH_2Cl_2$), 133 g of aluminum chloride and 105 g of

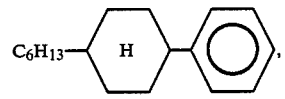

and were stirred. Thereto was added dropwise 51 g of glutaric anhydride

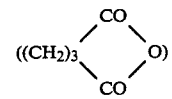

at room temperature, after which the resulting solution was allowed to reaction at the same temperature for 7 hours. Thereafter, the reaction solution was poured into dilute hydrochloric acid. The $CH_2Cl_2$ layer was washed with water by decantation, and then dried. The $CH_2Cl_2$ was distilled off, and the residue was recrystallized to obtain

In another flask was placed 104 g of the reaction product, followed by adding thereto 300 ml of diethylene glycol ($HO(CH_2)_2O(CH_2)_2OH$), 44 g of 80% hydrazine hydrate ($NH_2—NH_2.H_2O$) and 40 g of a 50% aqueous potassium hydroxide (KOH) solution. The resulting solution was stirred at 120° to 130° C. for 3 hours, and then at 220° C. for 2 hours. After being cooled, the reaction solution was poured into water, and the thus obtained mixture was made acid with hydrochloric acid. The mixture was extracted with benzene, and the extract was washed with water and then dried. After the benzene was distilled off, the residue was recrystallized to obtain a white crystal of

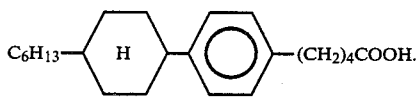

In another flask was placed 100 ml of THF, and 6.5 g of Li[AlH₄] was added thereto, after which the resulting mixture was stirred. A solution of 52 g of the

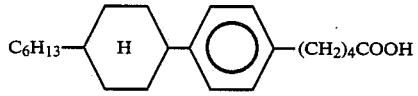

in 150 ml of THF was added dropwise to the mixture at room temperature. The thus obtained solution was stirred at room temperature for 3 hours, after which the reaction solution was poured into ice water and extracted with $(C_2H_5)_2O$. After the extract was washed with water and then dried, the $(C_2H_5)_2O$ was distilled off, and the residue was recrystallized to obtain

In 150 ml of benzene was dissolved the reaction product, and 31 g of $SOCl_2$ was then added thereto, after which the resulting mixture was refluxed for 5 hours and the surplus $SOCl_2$ was distilled off. The residue was poured into water and extracted with benzene. After the extract was washed with water and then dried, the benzene was distilled off, and the residue was recrystallized to obtain

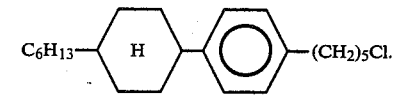

In further another flask was placed 150 ml of nonanol ($C_9H_{19}OH$), and 4.6 g of Na was completely dissolved therein. Thereafter a solution of 45 g of the

in 150 ml of $C_9H_{19}OH$ was added thereto dropwise. After completion of the addition, the resulting mixture was stirred at reflux temperature for 4 hours, and the $C_9H_{19}OH$ was distilled off under reduced pressure, after which the residue was distilled under reduced pressure and the distillate was recrystallized to obtain

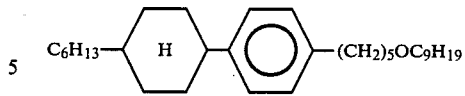

(Sample 39)

in a yield of 21 g.

The values of elementary analysis (C 84.05%, H 12.49%) of the sample 39 were in good agreement with the values calculated from the molecular weight for $C_{24}H_{40}O$. In the mass spectrum, a peak of ion of the molecule appeared at a m/e ratio of 456. Further, in the infrared absorption spectrum, an absorption band of the ether linkage appeared at 1120 cm⁻¹. From the relation between these facts and the starting compounds, the sample 39 was identified as the liquid crystalline compound of the above formula.

Colorless liquid crystallized compounds represented by the above general formula can be produced in the same manner as above by properly selecting the number of carbon atoms $R^4$ in the starting material

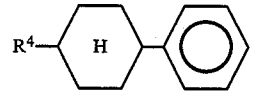

and the number of carbon atoms of $R^5$ in the alcohol $R^5OH$ used for etherification.

EXAMPLE 12

(Process for producing a colorless liquid crystalline compound represented by the general formula:

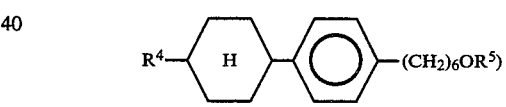

In a flask were placed 400 ml of $CH_2Cl_2$, 130 g of $AlCl_3$ and 200 g of

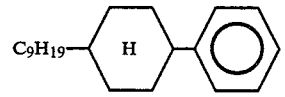

and mixed. Thereto was added dropwise 58 g of adipic anhydride

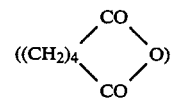

at room temperature, after which the resulting mixture was stirred at the same temperature for 8 hours. Thereafter, this reaction mixture was added to dilute hydrochloric acid, washed with water by decantation, and then dried, and the $CH_2Cl_2$ was distilled off. The residue was recrystallized to obtain

In another flask, 120 g of the reaction product, 400 ml of HO(CH$_2$)$_2$O(CH$_2$)$_2$OH, 45 g of 80% H$_2$N—NH$_2$·H$_2$O and 40 g of a 50% aqueous KOH solution were mixed, and allowed to react at 130° C. for 3 hours and then at 230° C. for 2 hours. The reaction mixture was cooled and then poured into water, and the resulting mixture was made acid with hydrochloric acid and then extracted with benzene. The extract was washed with water and then dried. After the benzene was distilled off, the residue was recrystallized to obtain a white crystal of

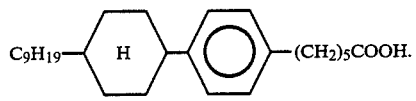

In further another flask were placed 200 ml of THF and 6.5 g of Li[AlH$_4$] and stirred. A solution of 60 g of the

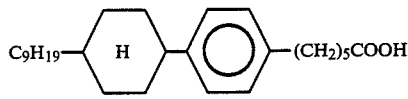

in 300 ml of THF was added thereto dropwise at room temperature. The resulting mixture was allowed to react at room temperature for 3 hours, poured into ice water, and then extracted with (C$_2$H$_5$)$_2$O. The extract was washed with water and then dried, after which the (C$_2$H$_5$)$_2$O was distilled off, and the residue was recrystallized to obtain

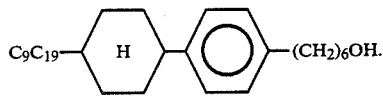

To a solution of 50 g of the reaction product in 200 ml of benzene was added 35 g of SOCl$_2$, after which the resulting mixture was refluxed for 5 hours and the surplus SOCl$_2$ was distilled off. The residue was poured into water and extracted with benzene. The extract was washed with water and then dried, after which the benzene was distilled off, and the residue was recrystallized to obtain

In still another flask was placed 200 ml of C$_9$H$_{19}$OH, and 5 g of Na was completely dissolved therein, after which the resulting solution was refluxed. A solution of 40 g of the

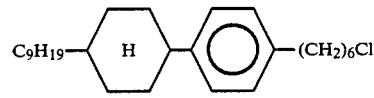

in 250 ml of C$_9$H$_{19}$OH was added thereto dropwise, after completion of the addition, the resulting solution was refluxed continuously for 8 hours. The solution after the reflux was washed with water and then dried, after which the C$_9$H$_{19}$OH was distilled off, and the residue was distilled under reduced pressure and the distillate was recrystallized to obtain (Sample 40)

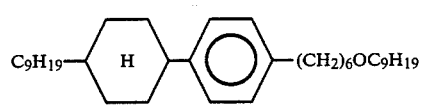

in a yield of 26 g.

The values of elementary analysis (C 84.30%, H 12.59%) of the sample 40 were in good agreement with the values calculated from the molecular weight for C$_{36}$H$_{64}$O. In the mass spectrum, a peak of ion of the molecule appeared at a m/e ratio of 512. Further, in the infrared absorption spectrum, an absorption band of the ether linkage appeared at 1120 cm$^{-1}$. From the relation between these facts and the starting compounds, the sample 40 was identified as the liquid crystalline compound of the above formula.

Colorless liquid crystalline compounds represented by the above general formula can be produced in the same manner as above by properly selecting the number of carbon atoms of R$^4$ in the starting material

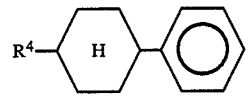

and the number of carbon atoms of R$^5$ in the alcohol R$^5$OH used for etherification.

EXAMPLE 13

(Process for producing a colorless liquid crystalline compound represented by the general formula:

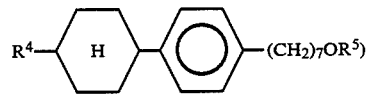

In a flask were placed 300 ml of CH$_2$Cl$_2$, 133 g of AlCl$_3$ and 99 g of

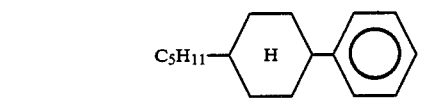

and mixed. Thereinto was added 64 g of pimelic anhydride

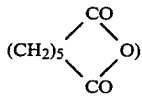

at room temperature, after which the resulting mixture was refluxed at the same temperature for 9 hours. Thereafter, the reaction mixture was poured into dilute hydrochloric acid and the $CH_2Cl_2$ layer was washed with water by decantation. Further, it was dried, and the $CH_2Cl_2$ was distilled off, after which the residue was recrystallized to obtain

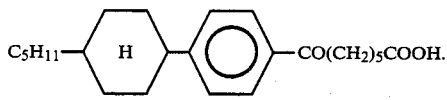

In another flask, 108 g of the reaction product, 300 ml of $HO(CH_2)_2O(CH_2)_2OH$, 44 g of 80% $H_2N-NH_2 \cdot H_2O$ and 40 g of a 50% aqueous KOH solution were mixed, and stirred at 130° C. for 3 hours and then at 230° C. for 3 hours. The reaction mixture was cooled and then poured into water, after which the resulting mixture was made acid with hydrochloric acid and extracted with benzene. The extract was washed with water and then dried, and the benzene was distilled off. The residue was recrystallized from ligroin to obtain a white crystal of

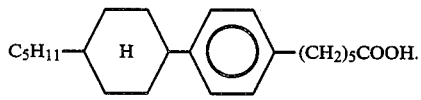

In further another flask were placed 100 ml of THF and 6.5 g of $Li[AlH_4]$ and stirred. A mixed solution of 54 g of the

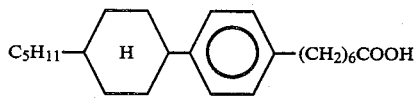

and 200 ml of THF was gradually added thereto dropwise at room temperature. The resulting solution was stirred at room temperature for 3 hours, after which this reaction solution was poured into ice water and extracted with $(C_2H_5)_2O$. The extract was washed with water and then dried, after which the $(C_2H_5)_2O$ was distilled off and the residue was recrystallized from n-hexane (n—$C_6H_{14}$) to obtain

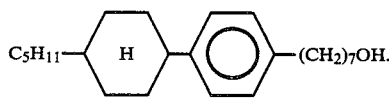

In 100 ml of benzene was completely dissolved 45 g of this reaction product. To the resulting solution was added 36 g of $SOCl_2$, after which the resulting mixture was refluxed for 5 hours, and the surplus $SOCl_2$ was removed. The residue was poured into water and extracted with benzene. The extract was washed with water and then dried, and the benzene was distilled off, after which the residue was recrystallized from $C_6H_{14}$ to obtain

In still another flask was placed 200 ml of decanol ($C_{10}H_{21}OH$), and 7 g of Na was completely dissolved therein, after which a solution of 36.5 g of the

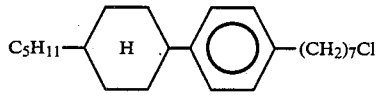

in 200 ml of $C_{10}H_{21}OH$ was added thereto dropwise. After the addition, the resulting solution was refluxed for 3 hours, and this reaction mixture was cooled, after which $(C_2H_5)_2O$ was further added thereto. Subsequently, the thus obtained mixture was washed with water and then dried, after which the $(C_2H_5)_2O$ and $C_{10}H_{21}OH$ was distilled off, and the residue was distilled under reduced pressure. The main distillate was recrystallized to obtain (Sample 41)

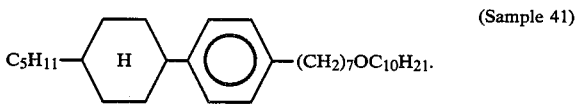

The values of elementary analysis (C 84.24%, H 12.49%) of the sample 41 were in good agreement with the values calculated from the molecular weight for $C_{34}H_{60}O$. In the mass spectrum, a peak of ion of the molecule appeared at a m/e ratio of 485. Further, in the infrared absorption spectrum, an absorption band of the ether linkage appeared at 1120 cm$^{-1}$. From the relation between these facts and the starting compounds, the sample 41 was identified as the liquid crystalline compound of the above formula.

Colorless liquid crystalline compounds represented by the above general formula can be produced in the same manner as above by properly selecting the number of carbon atoms of $R^4$ in the starting material

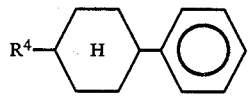

and the number of carbon atoms of $R^5$ in the alcohol $R^5OH$ used for etherification.

EXAMPLE 14

(Process for producing a colorless liquid crystalline compound represented by the general formula:

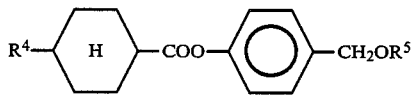

and its physical properties)
In a flask were placed 50 g of

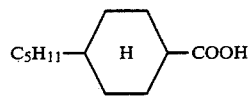

and 60 g of $SOCl_2$ and stirred at 60° C. for 8 hours. Thereafter, the surplus $SOCl_2$ was removed, and 52 g of

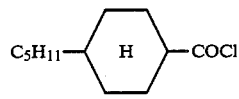

was obtained by distilling the residue under reduced pressure.

Next, 28 g of

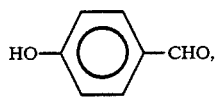

40 ml of pyridine and 150 ml of benzene were placed in another flask, and 52 g of the

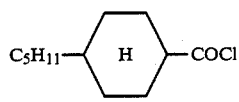

was gradually added thereto dropwise with stirring. After completion of the addition, the resulting mixture was stirred continuously for 1 hour. The deposited hydrochloride of pyridine was removed by filtration, and 59 g of

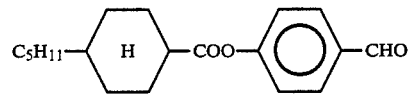

was obtained by distilling the residue under reduced pressure.

In further another flask were placed 6 g of $Na[BH_4]$ and 300 ml of $C_2H_5OH$ and vigorously stirred. Simultaneously with the vigorous stirring, 59 g of

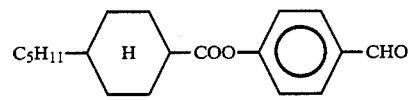

was added to the resulting mixture while maintaining the temperature of the mixture at 40° C. or lower. After continuous stirring for 4 hours, 10 ml of $CH_3COOH$ was added thereto dropwise. The thus obtained mixture was poured into about 1 Kg of ice to deposit

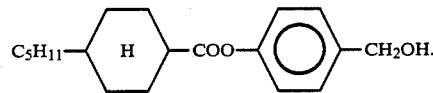

It was thoroughly washed with water to obtain 40 g of

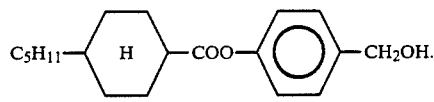

Subsequently, 20 g of $SOCl_2$ was added to 40 g of the

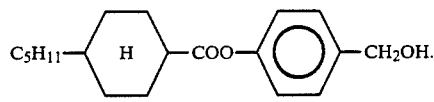

and the resulting mixture was refluxed for 2 hours. Thereafter, the surplus $SOCl_2$ was removed, and the residue was distilled under reduced pressure to obtain 40 g of

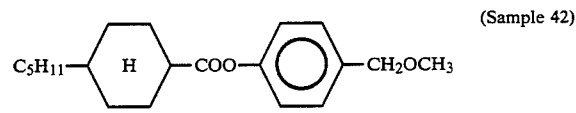

In still another flask were placed 100 ml of methyl alcohol ($CH_3OH$) and 3 g of Na, and Na was completely dissolved therein. Thereafter, 40 ml of pyridine was added, followed by adding thereto 40 g of

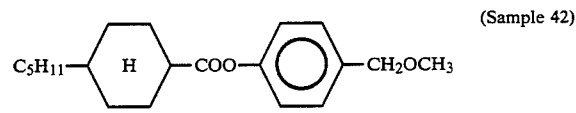

and the resulting mixture was refluxed continuously for 20 hours. Crude

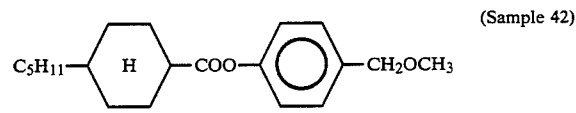

was obtained by distilling the mixture under reduced pressure, after which (Sample 42)

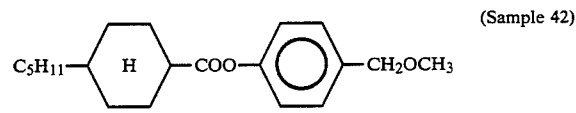

was obtained by recrystallization from $CH_3COCH_3$.

Figure 10:
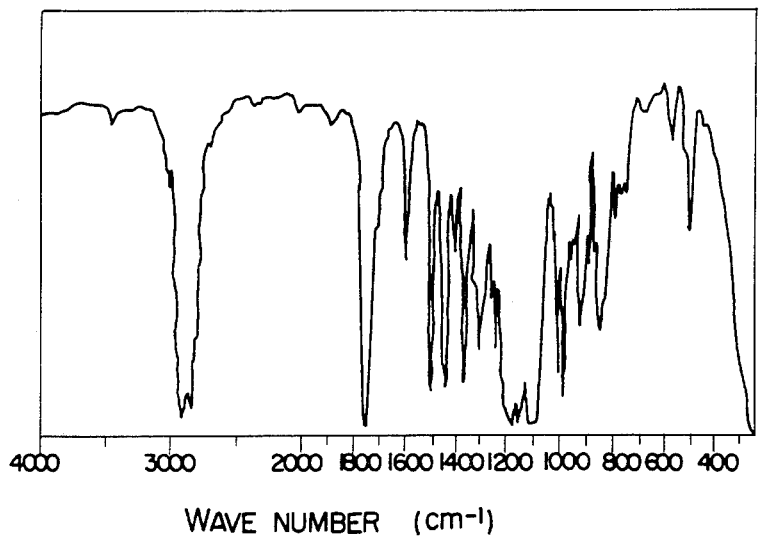

The values of elementary analysis (C 75.23%, H 9.61%) of the sample 42 were in good agreement with the values calculated from the molecular weight (C 74.43%, H 9.63%) for $C_{20}H_{30}O_3$. In addition, the infrared absorption spectrum of the sample 42 was as shown in FIG. 10, and an absorption band of the ether linkage appeared at 1100 $cm^{-1}$ and that of the ester linkage at 1750 $cm^{-1}$. From the relation between these two facts and the starting compound the sample 42 was identified as the liquid crystalline compound of the above formula.

There were shown in Table 4 the phase transition temperatures of the sample 42 and other samples obtained by a production process according to that of the sample 42.

TABLE 4

| Sample | $R^4$ | $R^5$ | C-I | C-N | N-I |
|---|---|---|---|---|---|
| 42 | $C_5H_{11}$ | $CH_3$ | 53.5 | — | (42) |
| 43 | $CH_3$ | $C_3H_7$ | −1 | 3 | — |
| 44 | $C_2H_5$ | $C_3H_7$ | −5 | 4 | — |
| 45 | $C_3H_7$ | $CH_3$ | 23 | — | (13) |
| 46 | $C_3H_7$ | $C_3H_7$ | 4 | — | (−15) |
| 47 | $C_4H_9$ | $C_3H_7$ | −3 | 3 | — |
| 48 | $C_5H_{11}$ | $C_3H_7$ | 7 | — | (4.5) |
| 49 | $C_5H_{11}$ | $C_4H_9$ | 10 | — | (−3) |
| 50 | $C_5H_{11}$ | $C_5H_{11}$ | 7 | — | (3) |
| 51 | $C_5H_{11}$ | $C_6H_{13}$ | 12 | — | (10) |
| 52 | $C_5H_{11}$ | $C_7H_{15}$ | 36 | — | (29) |
| 53 | $C_7H_{15}$ | $CH_3$ | 49 | — | (34) |
| 54 | $C_7H_{15}$ | $C_2H_5$ | 19 | — | (19) |
| 55 | $C_7H_{15}$ | $C_3H_7$ | 19 | — | (14) |
| 56 | $C_7H_{15}$ | $C_8H_{17}$ | 39 | — | (20) |

There can be produced

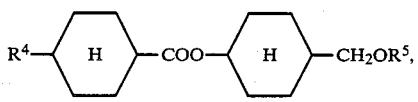

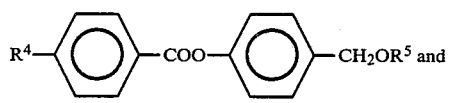

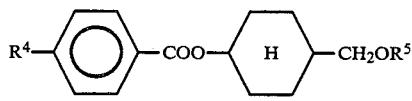

by a production process according to that described in the present example.

EXAMPLE 15

(Process for producing a colorless liquid crystalline compound represented by the general formula:

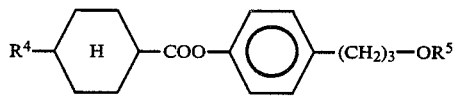

and its physical properties)

In 600 ml of $CH_3OH$ was dissolved 20 g of Na, and 120 g of 3-bromopropylbenzene was added dropwise with heating under reflux. After aging under reflux for 6 hours, the reaction solution was poured into 2 liters of ice water, and the separated oil layer was extracted with benzene. The benzene was distilled off, after which the residue was distilled under reduced pressure to obtain 3-methoxypropylbenzene. The boiling point of this compound was 96°–98° C/15 mmHg.

Next, 195 g of $AlCl_3$ and 100 g of 3-methoxypropylbenzene were poured into 1.5 liters of $CH_2Cl_2$, and the resulting mixture was cooled with ice under stirring. Thereto was gradually added dropwise 79 g of acetyl chloride ($CH_3COCl$), and the thus obtained mixture was stirred under ice-cooling continuously for 6 hours. After the termination of the evolution of hydrogen chloride (HCl) gas was ascertained, the reaction solution was poured into 1 liter of dilute hydrochloric acid, and the $CH_2Cl_2$ layer was separated, after which the $CH_2Cl_2$ was distilled off, and the residue was distilled under reduced pressure to obtain p-(3-methoxypropyl)acetophenone. The boiling point of this compound was 94–95° C./0.3 mmHg.

67 Grams of the p-(3-methoxypropyl)acetophenone and 620 ml of 88% formic acid (HCOOH) were mixed and stirred, after which 310 ml of acetic anhydride (($CH_3CO)_2O$), 4 ml of concentrated sulfuric acid, and 110 ml of a 35% aqueous hydrogen perioxide solution were added thereto dropwise in that order. The resulting solution was heated to a temperature of 40° to 50° C. and then stirred for 8 hours, after which this reaction solution was poured into water. The separated oil layer was extracted, and the solvent was distilled off, after which 100 ml of $CH_3OH$ and 250 ml of a 2N aqueous sodium hydroxide solution were added to the residue, and the thus obtained solution was heated and refluxed for 2 hours. After being cooled, this reaction solution was made acid with hydrochloric acid to separate oil layer. The oil layer was extracted with benzene, and the benzene was distilled off, after which the residue was distilled under reduced pressure to obtain p-(3-methoxypropyl)phenol. The boiling point of this compound was 106°–108° C./10 mmHg. In a mixture of 100 ml of benzene and 5 ml of pyridine was dissolved 10 g of the p-(3-methoxypropyl)phenol, and 14 g of p-(3-methoxypropyl)phenyl 4-pentylcyclohexane carboxylate was added thereto dropwise, and the resulting solution was stirred at room temperature continuously for 3 hours. This reaction solution was poured into water and extracted with benzene, and the benzene was distilled off, after which the residue was recrystallized from $CH_3COCH_3$.

Figure 11:
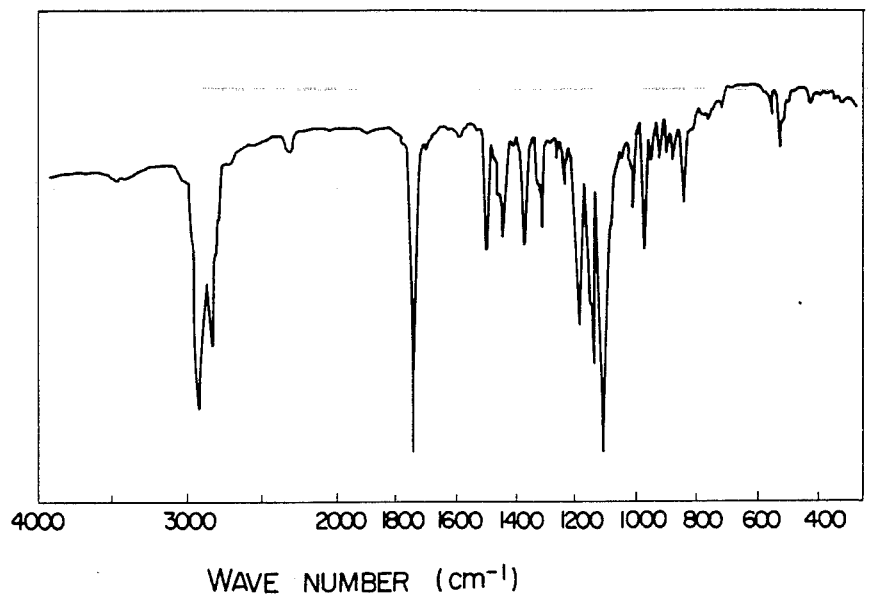

The infrared absorption spectrum of the compound obtained in the manner described above showed an absorption band of an ester linkage at 1750 cm$^{-1}$ and that of an ether linkage at 1120 cm$^{-1}$ as shown in FIG. 11. In the mass spectrum, a peak of ion of the molecule appeared at a m/e ratio of 346. From the relation between these two facts and the starting compound, the compound synthesized here was identified as p-(3-methoxypropylphenyl)-4'-pentylcyclohexylcarboxylate:

(Sample 57)

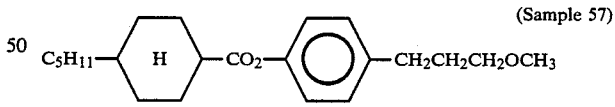

The melting point of the sample 57 was 42° C. and its phase transition temperature was 32° C. for (I-N) transition.

Colorless liquid crystalline compounds represented by the above general formula can be produced in the same manner as mentioned above by changing the respective numbers of carbon atoms of $R^4$ and $R^5$ in the starting compounds. Further, the compound represented by the above general formula can most easily be produced by a combined process of Williamson's synthesis of ether, Friedel-Crafts reaction and Baeyer-Villiger process.

Among values showing physical properties of liquid crystal materials, there is optical anisotropy (hereinafter referred to as Δn, which is the difference between the refractive indexes for abnormal light and normal light). Δn is greatly concerned with the display properties of liquid crystal display elements, and a liquid crystal having a large Δn or that having a small Δn is desired depending upon the difference of driving method. It is well known about the difference in refractive index that when these liquid crystals are used, the display properties of liquid crystal display element can be improved. It was confirmed that in the case of the liquid crystalline compound of the present example, Δn can be varied by varying the distance between the benzene ring and the oxygen atom. The colorless liquid crystalline compound of the present example also makes Δn of a liquid crystal composition still smaller.

EXAMPLE 16

(Process for producing a colorless liquid crystalline compound represented by the general formula:

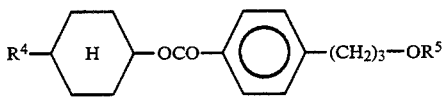

and its physical properties)

In a flask were placed 500 ml of $CH_2Cl_2$, 80 g of $AlCl_3$ and 130 g of 4-pentylcyclohexane carbonyl chloride and stirred. Thereafter, 100 g of (3-bromopropyl)-benzene was added dropwise with ice-cooling. After 6 hours, the reaction solution was poured into dilute hydrochloric acid to decompose the complex. The $CH_2Cl_2$ layer was washed with water, dehydrated and them filtered, after which the $CH_2Cl_2$ was removed, and the residue was recrystallized from ligroin to obtain 4-pentylcyclohexyl-p-(3-bromopropyl)phenyl ketone. The melting point of this compound was 38° to 39° C.

In another flask were placed 40 g of 4-pentylcyclohexyl-p-(3-bromopropyl)phenyl ketone and 200 ml of $CH_3OH$ and stirred. Thereafter, a sodium methylate-methanol solution prepared by dissolving 3.5 g of Na in 80 ml of absolute $CH_3OH$ was added thereto dropwise, and the resulting solution was refluxed. After 6 hours, the reaction solution was concentrated and then poured into water, after which the separated oil layer was extracted with benzene. After the benzene was distilled off, the residue was distilled under reduced pressure to obtain 4-pentylcyclohexyl-p-(3-methoxypropyl)phenyl ketone. The boiling point of this compound was 168°–171° C./0.08 mmHg.

In further another flask, 24 g of the 4-pentylcyclohexyl-p-(3-methoxypropyl)phenyl ketone and 130 ml of 88% HCOOH were mixed and stirred. Subsequently, 65 ml of $(CH_3CO)_2O$, 1 ml of concentrated sulfuric acid and 20 ml of a 35% aqueous hydrogen peroxide solution were added thereto dropwise in that order. The resulting solution was heated to 40° to 50° C. and stirred for 13 hours, after which this reaction solution was poured into water. The separated oil layer was extracted with benzene and the solvent was distilled off, after which the residue was distilled under reduced pressure, and the distillate was recrystallized from $CH_3OH$.

The boiling point of the thus obtained compound was 181°–188° C./0.15 mmHg.

Figure 12:
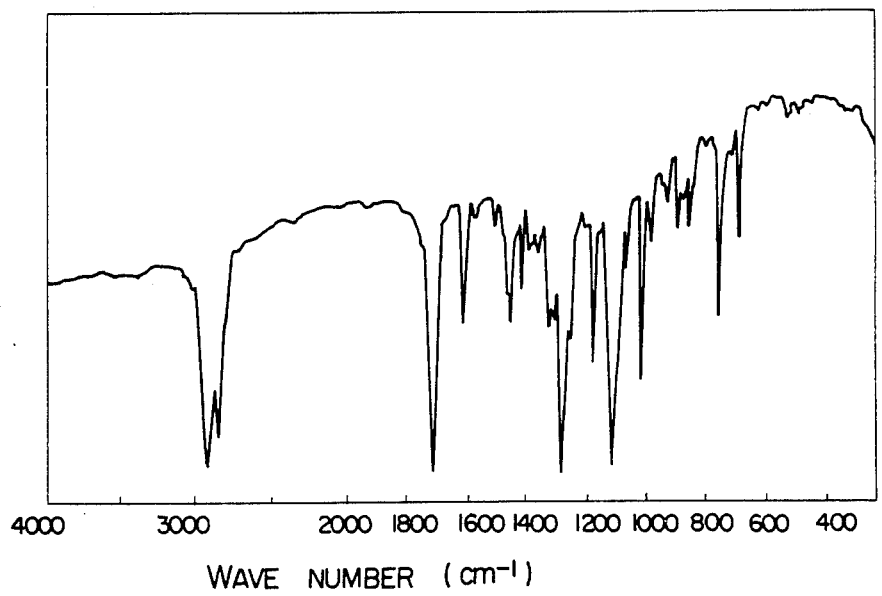
Figure 13:
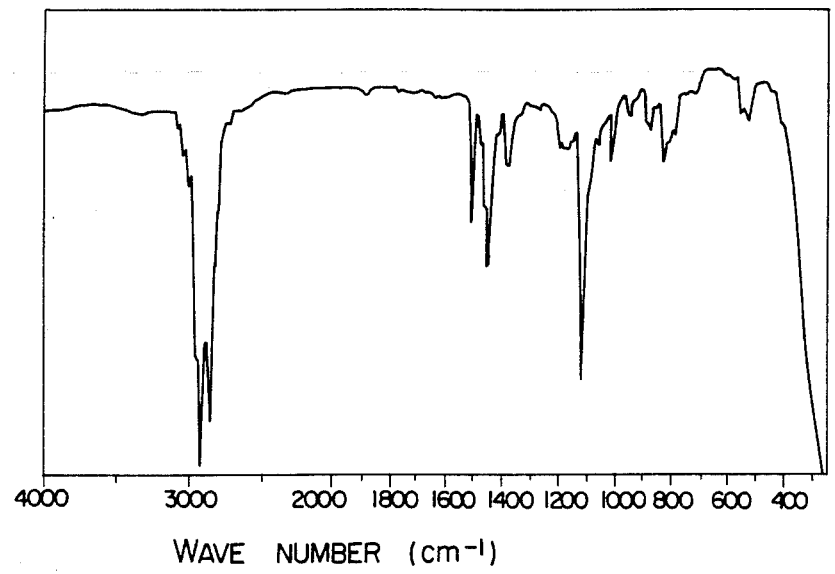
Figure 14:
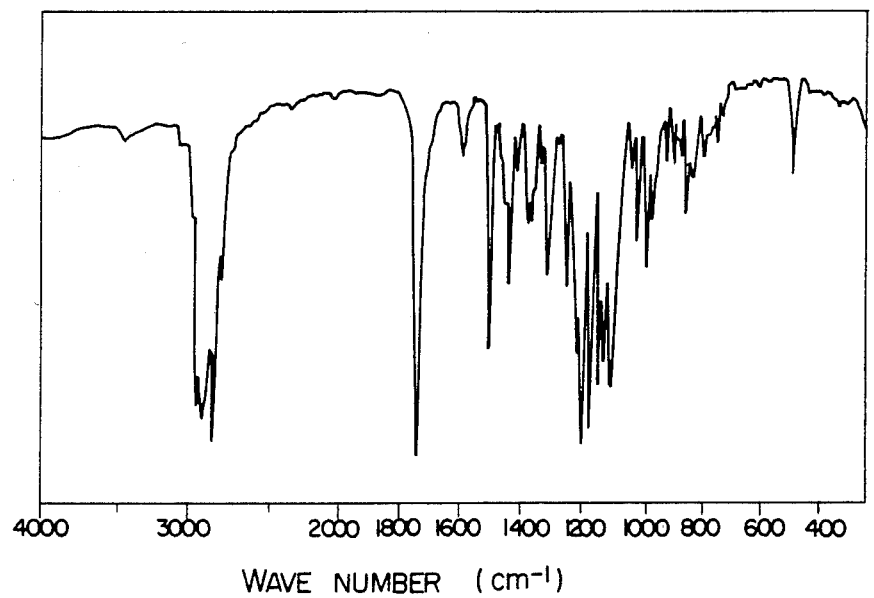
Figure 15:
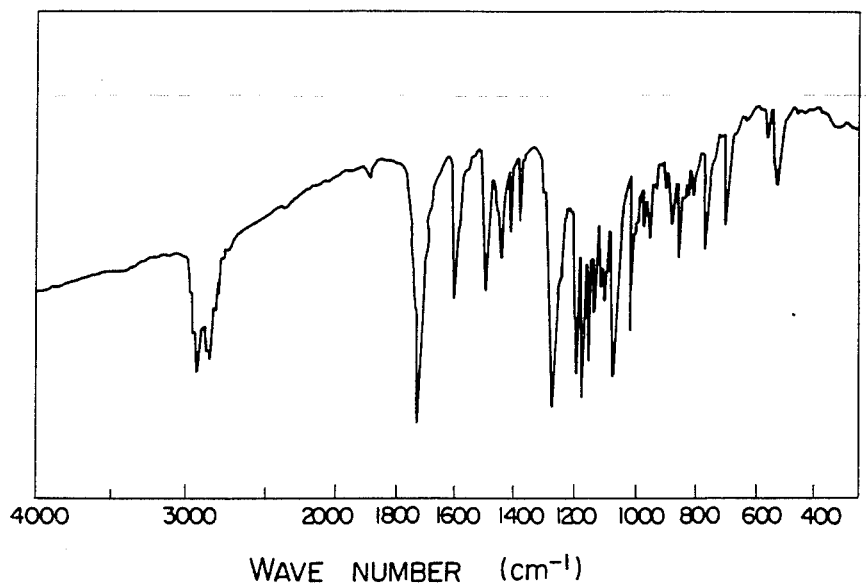

The infrared absorption spectrum of the compound obtained in the manner described above had an absorption band of an ester linkage at 1720 $cm^{-1}$ and that of an ether linkage at 1120 $cm^{-1}$ as shown in FIG. 12. In the mass spectrum, a peak of ion of the molecule appeared at a m/e ratio of 346. From the relation between these two facts and the starting compounds, the compound synthesized here was identified as 4-pentylcyclohexyl p-(3-methoxypropyl)benzoate:

(Sample 58)

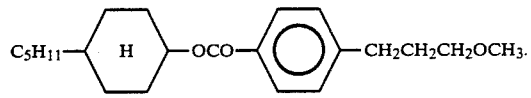

The melting point of the sample 58 was 30° C. and its phase transition temperature was 13° C. for (I–N) transition.

Colorless liquid crystalline compounds represented by the above general formula can be produced in the same manner as above by properly selecting the respective numbers of carbon atoms of $R^4$ and $R^5$.

Like the compound of Example 15, the colorless liquid crystalline substance of the present example is a compound which also makes Δn of a liquid crystal composition still smaller.

EXAMPLE 17

(Process for producing a colorless liquid crystalline compound represented by the general formula:

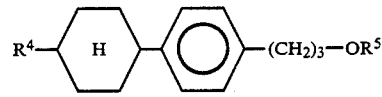

and its physical properties)

To a mixture of 40 g of p-(4-pentylcyclohexyl)acetophenone, 20 g of thallium nitrate ($Tl(NO_3)_3$) and 87 g of 70% perchloric acid was added 300 ml of $CH_3OH$, and the resulting mixture was stirred at room temperature for 4 hours. Thereafter, it was filtered, and the filtrate was extracted with benzene, after which the benzene layer was washed with water and dried. Then the benzene was distilled off and the residue was recrystallized from $CH_3OH$ to obtain the objective compound methyl p-(4-pentylcyclohexyl)phenylacetate. The compound had a melting point of 46° to 47° C.

Next, 400 ml of $(C_2H_5)_2O$ was added to 6 g of Li-[$AlH_4$], and the resulting mixture was stirred. Thereto was very gradually added dropwise a $(C_2H_5)_2O$ solution including 36 g of the aforesaid methyl p-(4-pentylcyclohexyl)phenylacetate, and after completion of the addition, the thus obtained mixture was stirred at 30° C. or lower continuously for 3 hours. The mixture was then poured into dilute hydrochloric acid and extracted with $(C_2H_5)_2O$. After the $(C_2H_5)_2O$ was distilled off, the residue was recrystallized from n—$C_6H_{14}$ to obtain 4-[p-(2-hydroxyethyl)phenyl]pentylcyclohexane. The melting point of this compound was 44° to 46° C.

To 20 g of the compound were added 18 g of $SOCl_2$, 0.6 g of pyridine and 300 ml of benzene, and the resulting mixture was refluxed for 5 hours. After the surplus $SOCl_2$ was distilled off, the residue was distilled to obtain 4-[p-(2-chloroethyl)phenyl]pentylcyclohexane. The boiling point of this compound was 174°–176° C./1 mmHg.

9 Grams of the 4-]p-(2-chloroethyl)phenyl]pentylcyclohexane, 100 ml of dimethyl sulfoxide (($CH_3)_2SO$) and 23 g of sodium cyanide (NaCN) were stirred together at 140° to 150° C. for 2 hours. After the resulting mixture was cooled, a 10% aqueous sodium hypochlorite (NaClO) solution was added. Further, water was added thereto, and the precipitate was recrystallized from ligroin to obtain 4-[p-(2-cyanoethyl)phenyl]pentylcyclohexane. The melting point of this compound was 44° to 46° C.

To 6 g of the compound were added 11 g of KOH, 80 ml of water and 130 ml of $C_2H_5OH$, and the resulting mixture was refluxed for 10 hours. The $C_2H_5OH$ was distilled off, after which the residue was extracted with $(C_2H_5)_2O$, and the extract was washed with water. After the $(C_2H_5)_2O$ was distilled off, the residue was recrystallized from ligroin to obtain 4-[p-(2-hydroxycarbonyl)phenyl]pentylcyclohexane. It was confirmed that this compound had a liquid crystal phase in a temperature range from 128.8° to 164.3° C.

Next, 0.82 g of $Li[AlH_4]$ was added to 50 ml of dried $(C_2H_5)_2O$, and the resulting mixture was stirred. Thereto was gradually added 5 g of 4-[p-(2-hydroxycarbonylethyl)phenyl]pentylcyclohexane. Thereafter the thus obtained mixture was stirred for 5 hours, and filtered. The $(C_2H_5)_2O$ was distilled off from the filtrate, and the residue was recrystallized from n—$C_6H_{14}$ to obtain 4-[p-(3-hydroxypropyl)phenyl]pentylcyclohexane. The melting point of this compound was 70.7° to 72.5° C. To a mixture of 3.6 g of $SOCl_2$, one drop of pyridine and 50 ml of benzene was added 4.3 g of the 4-[p-(3-hydroxypropyl)phenyl]pentylcyclohexane obtained above, and the resulting mixture was refluxed for 5 hours. Thereafter, the surplus $SOCl_2$ was distilled off to obtain 4-[p-(3-chloropropyl)phenyl]pentylcyclohexane. The melting point of this compound was 70.7° to 72.5° C.

Subsequently, 1 g of Na was dissolved in 50 ml of dried $CH_3OH$. Thereto was added 4.3 g of the 4-[p-(3-chloropropyl)phenyl]pentylcyclohexane obtained above. The resulting mixture was refluxed for 62 hours, after which the $CH_3OH$ was distilled off, and the residue was poured into water, and then the oil layer was extracted with benzene, and the extract was dried, the benzene was distilled off and the obtained residue was recrystallized.

The infrared absorption spectrum of the compound obtained in the manner deseribed above had an absorption band of the ether linkage at 1120 $cm^{-1}$, and an additional absorption band of the —$CH_2$— group at 2800–3000 $cm^{-1}$. In the mass spectrum, a peak of ion of the molecule appeared at a m/e ratio of 302. From the relation between these two facts and the starting compounds, the compound synthesized here was identified as 4-[p-(3-methoxypropyl)phenyl]pentylcyclohexane:

(Sample 59)

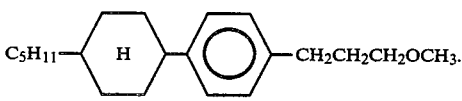

The melting point of the sample 59 was 2.0° C., and its phase transition temperature was −16° C. for (I-N) transition. Colorless liquid crystalline compounds represented by the above general formula can be produced in the same manner as above by changing the respective number of carbon toms of $R^4$ and $R^5$ in the starting compounds.

Like the compound of Example 15, the colorless liquid crystalline compound of the present example also makes Δn of a liquid crystal composition still smaller.

EXAMPLE 18

(Process for producing a colorless liquid crystalline compound represented by the general formula:

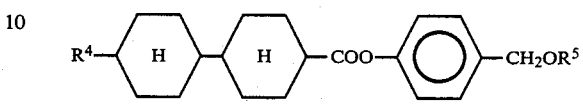

and its physical properties)

Dried bromine gas $(Br_2)$ was blown through a mixed solution of 33 g of p-hydroxybenzyl alcohol

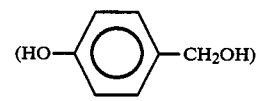

and 900 ml of benzene for 2 hours while cooling the solution with ice water. Thereafter, the solution was stirred for 2 hours, and then distilled to obtain p-hydroxybenzyl bromide

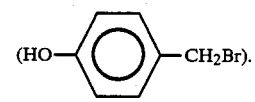

The boiling point of this compound was 125°–126° C./15 mmHg.

Next, 5 g of Na was dissolved in 300 ml of absolute $CH_3OH$, and about 25 g of the

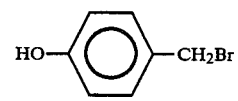

was added dropwise to the resulting solution while refluxing solution. The reaction mixture was refluxed continuously for 4 hours, and then poured into 1 liter of ice water. The separated oil layer was extracted with $(C_2H_5)_2O$, and the extract was dried. There was thus obtained p-(methoxymethyl)phenol.

On the other hand, 50 g of 4-propyl-4'-cyanobicyclohexane was dissolved in 50 ml of $C_2H_5OH$, and 25 g of KOH and 15 ml of water was added to the resulting solution, after which the resulting mixture was refluxed for 8 hours and poured into dilute hydrochloric acid, and then the acidic solution was extracted with $(C_2H_5)_2O$ and the $(C_2H_5)_2O$ was distilled off. The residue was recrystallized from benzene to obtain 4-propyl-4'-bicyclohexanecarboxylic acid.

To 100 ml of $SOCl_2$ was added 45 g of this compound, and the resulting mixture was stirred continuously for 8 hours while maintaining it at 50° C. Thereafter, it was distilled to obtain 4-propyl-4'-bicyclohexanecarbonyl chloride.

Next, 10 g of pyridine was added to 50 g of a solution (content: about 15%) of the previously obtained p-(methoxymethyl)phenol in 50 g of $(C_2H_5)_2O$, and the 4-propyl-4'-bicyclohexanecarbonyl chloride was added dropwise thereto.

Thereafter, the resulting mixture was refluxed for 2 hours and then washed with water, after which the (C₂H₅)₂O was distilled off, and the residue was recrystallized from CH₃COCH₃.

The infrared absorption spectrum of the compound obtained in the manner described above is shown in FIG. 14. It can be seen from FIG. 14 that an absorption band of the ester linkage appeared at 1750 cm⁻¹ and that of the ether linkage at 1100 cm⁻¹. In the mass spectrum, a peak of ion of the molecule appeared at a m/e ratio of 372. From the relation between these two facts and the starting compounds, the compound synthesized here was identified as p-methoxymethylphenyl 4-propyl-4'-bicyclohexanecarboxylate:

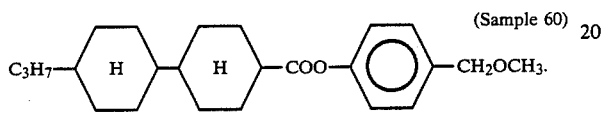
(Sample 60)

The phase transition temperature of this compound was 50° for (C-N) transition and 193° C. for (N-I) transition. The compound was very excellent in chemical stability.

A liquid crystalline compound corresponding to the above general formula can be produced by a production process according to that of the sample 60. That is to say,

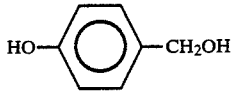

is first halogenated, and then converted into

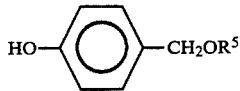

by using Williamson's synthesis process of ether. On the other hand,

was hydrolyzed to prepare a carboxylic acid, which was then halogenated into an acid halide. Esterification reaction of the acid halide with

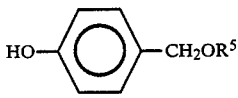

is effected, whereby a liquid crystalline compound of the above general formula is obtained.

As the starting material, there may be used

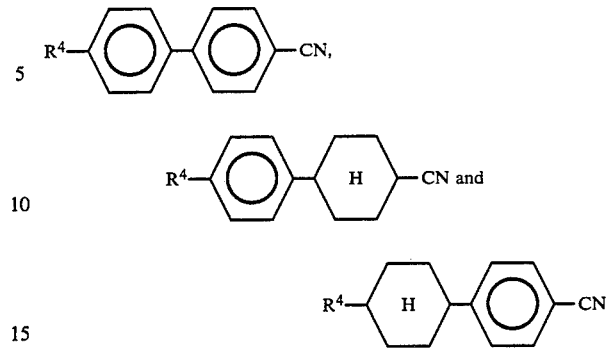

in addition to

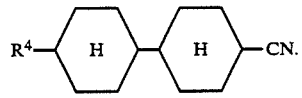

By properly selecting the starting material from these, there can be obtained, besides the liquid crystalline compound of the present example, colorless liquid crystalline compounds represented by the general formulas listed below.

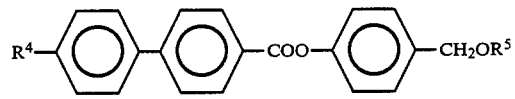

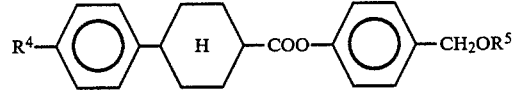

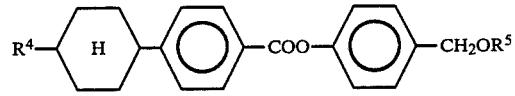

For example,

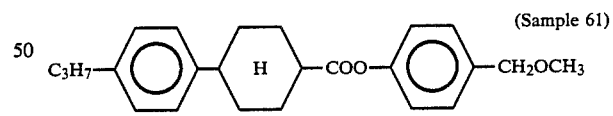
(Sample 61)

had a phase transition temperature of 82° C. for (C-N) transition and 139° C. for (N-I) transition, and

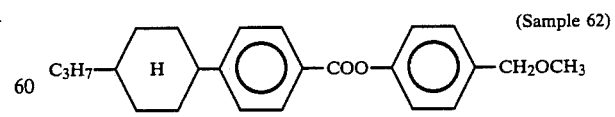
(Sample 62)

had a phase transition temperature of 90° C. for (C-N) transition and 173° C. for (N-I) transition.

EXAMPLE 19

(Process for producing a colorless liquid crystalline compound represented by the general formula:

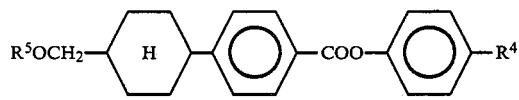

and its physical properties)

In a flask were placed 30.5 g of Li[AlH$_4$] and 200 ml of THF to obtain a suspension. One liter of a solution of 133 g of

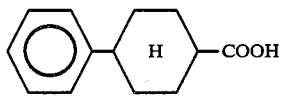

in THF was added dropwise with stirring under ice-cooling, and after completion of the addition, the resulting mixture was further stirred continuously for 2 hours. The reaction solution was poured into dilute hydrochloric acid and extracted with benzene. Thereafter the benzene was distilled off to obtain

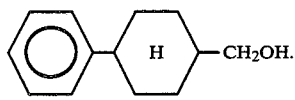

In 1.5 liters of (CH$_3$)$_2$SO were dissolved 123 g of the

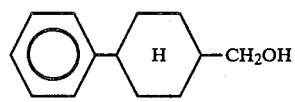

and 100 ml of 4% aqueous NaOH solution together with 700 g of methyl iodide (CH$_3$I), and the resulting solution was stirred at 60° C. for 2 hours, after which the reaction solution was poured into water and extracted with benzene, and the benzene was distilled off to obtain

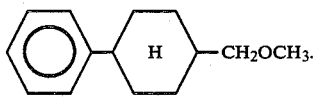

In another flask were placed 51.8 g of CH$_3$COCl, 500 ml of CH$_2$Cl$_2$ and 117 g of AlCl$_3$, and the resulting mixture was cooled with ice under stirring. Subsequently, 8.9 g of

was gradually added thereto dropwise, and the thus obtained solution was stirred under ice-cooling for 4 hours. This reaction solution was poured into 1 liter of dilute hydrochloric acid, and the CH$_2$Cl$_2$ layer was washed with water and the CH$_2$Cl$_2$ was distilled off, after which the residue was distilled under reduced pressure to obtain

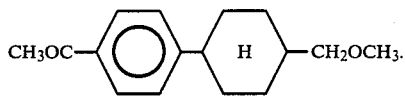

In further another flask, 500 ml of dioxane and 50 g of the

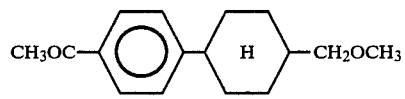

were placed. 1 Liter of 10% aqueous sodium hypobromite (NaBrO) solution was added dropwise thereto at room temperature with stirring. This reaction solution was poured into water and acidified with dilute hydrochloric acid, and was extracted with benzene. And the benzene was distilled off to obtain

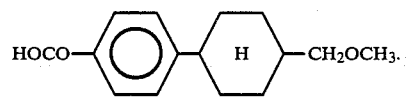

Thereafter, 100 g of SOCl$_2$ was added dropwise to 30 g of the

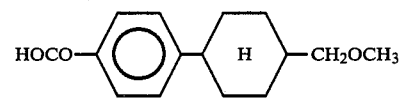

under ice-cooling, and the resulting mixture was stirred for 4 hours to obtain

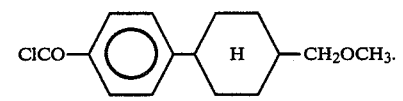

Further, 10 g of pyridine was added to 30 g of a solution (content: 30%) of

in benzene, and 8 g of the

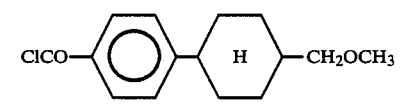

obtained above was added thereto dropwise. Thereafter, the resulting mixture was refluxed for 2 hours and then washed with water, after which the benzene was distilled off, and the residue was recrystallized from n—C$_6$H$_{14}$ and C$_2$H$_5$OH.

The infrared absorption spectrum of the compound obtained in the manner described above is shown in FIG. 15. It can be seen from FIG. 15 that an absorption band of the ester linkage appeared at 1,750 cm$^{-1}$ and that of the ether linkage at 1,100 cm$^{-1}$. From the relation between these two facts and the starting compounds, the compound synthesized here was identified as p-propylphenyl p-[4-(methoxymethyl)cyclohexyl]-benzoate:

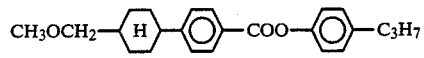 (Sample 63)

The phase transition temperature of this compound was 103° C. for (C-N) transition and 166° C. for (N-I) transition.

Liquid crystalline compounds corresponding to the above general formula can be produced by a production process according to that of the sample 63. That is to say,

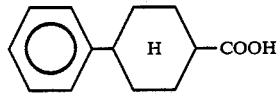

is first reduced into an alcohol. Subsequently, the alcohol was subjected to etherification, acetylation, haloform reaction and halogenation in that order to obtain an acid halide

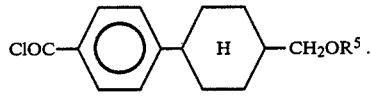

Next esterification of the acid halide with

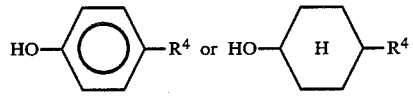

is effected to obtain the object compound:

Besides

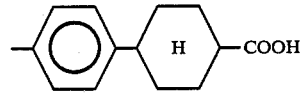

is first esterified to

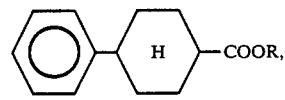

subsequently the ester is subjected to formylation, reduction, halogenation and etherification in order to obtain

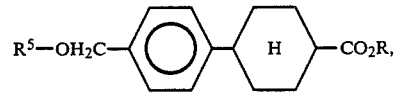

and then

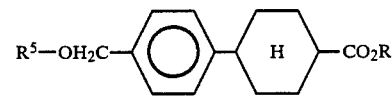

is hydrolized and halogenated to

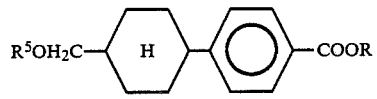

obtained as an intermediate in the above-mentioned process is used to produce bicyclohexane derivatives. That is to say, those both are hydrogenated to

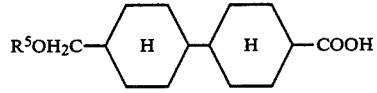

and halogenated to

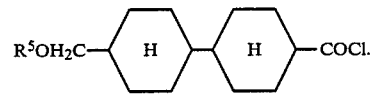

is obtained by using

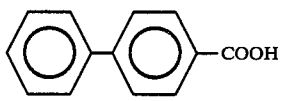

as a starting material according to the same process as mentioned in Example 19. These obtained acid chlorides are reacted with

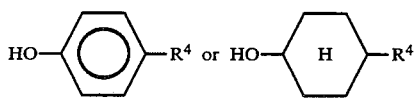

to obtain the following colorless liquid crystalline compounds besides the colorless liquid crystalline compound of the present Example.

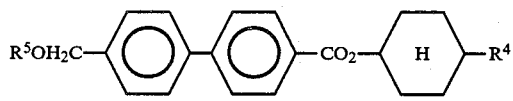

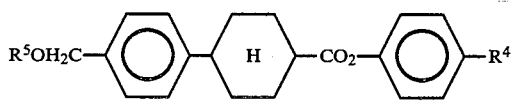

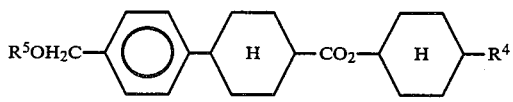

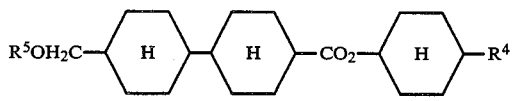

As compounds having, like the compound of the present example, three 6-membered rings and an ester group, there have heretofore known

(phase transition temperature: 93° C. for (C-N) transition and 189° C. for (N-I) transition) and

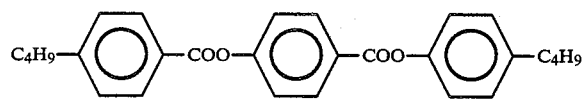

(phase transition temperature: 89° C. for (C-N) transition and 183° C. for (N-I) transition). Liquid compositions containing any of these conventional compounds have a wide mesomorphic range including room temperature, however they are disadvantageous in that they have a high viscosity. The cause of their high viscosity is presumed to be that in the compounds two ester groups are directly linked to three benzene rings, so that the oxygen atoms have a great polarizing effect. The cause why the compounds extends the mesomorphic range is thought to be that owing to the polarizing effect, the intermolecular interaction has such an intensity that the compounds are liable to become a liquid crystal. In contrast to the conventional compounds, the liquid crystalline compound of this invention extends the mesomorphic range of a liquid crystal composition and lowers its viscosity because in said compound, ester groups having a great polarizing effect is decreased and an ether group effective for lowering the viscosity is contained at the end.

EXAMPLE 20

(Process for producing a colorless liquid crystalline compound represented by the general formula:

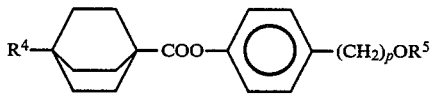

(wherein p is an integer of 1 to 6), and its physical properties)

In a flask, 600 g of 2-octanone ($CH_3(CH_2)_5COCH_3$), 500 g of tert-butanol (($CH_3)_3COH$) and 30 g of a $KOH/CH_3OH$ solution were mixed and then stirred under ice-cooling. To the resulting solution was added dropwise a solution of 375 g of acrylonitrile ($CH_2$=CHCN) in 400 g of ($CH_3)_3COH$ while maintaining the temperature at 5° C. or lower. After completion of the addition, the resulting solution was further stirred continuously for 1 hour, after which this reaction solution was made neutral by addition of dilute hydrochloric acid. The deposited salt was separated by filtration, and the residue was distilled under reduced pressure to obtain 3-acetyl-1,5-dicyano-3-pentylpentane.

Into 400 g of a 20% aqueous NaOH solution was poured 232 g of the reaction product, and the resulting mixture was heated and stirred for 8 hours. Subsequently, the mixture was made slightly acidic with dilute hydrochloric acid and then extracted with chloroform ($CHCl_3$). The solvent was distilled off to obtain 4-acetyl-4-pentyl-1,7-heptanedioic acid.

In 750 ml of ($CH_3CO)_2O$ was dissolved 130 g of this reaction product, and the resulting mixture was heated and refluxed for 3 hours and then distilled under reduced pressure to obtain 4-acetyl-4-pentylcyclohexanone.

To 600 ml of a 10% aqueous KOH solution was poured 70 g of this reaction product, and the resulting mixture was heated and refluxed for 5 hours. After cooled, the mixture was made neutral by addition of dilute hydrochloric acid and then extracted with ($C_2H_5)_2O$. The ($C_2H_5)_2O$ was distilled off to obtain 1-hydroxy-4-pentyl-3-bicyclo(2,2,2)octanone.

In 130 ml of $NH_2$—$NH_2$ was dissolved 21 g of this reaction product, and the resulting solutoin was heated and refluxed for 5 hours. After the solution was cooled, 29 g of KOH and 180 ml of HO(CH$_2$)$_2$O(CH$_2$)$_2$OH were added thereto, and the resulting mixture was heated to 230° to 240° C. When the evolution of nitrogen gas (N$_2$) ceased, 1.7 liters of cold water was added, after which the thus obtained mixture was extracted with (C$_2$H$_5$)$_2$O. The (C$_2$H$_5$)$_2$O was distilled off to obtain 1-hydroxy-4-pentylbicyclo(2,2,2)octane.

Into a mixed solution of 160 g of hydrobromic acid and 40 g of concentrated sulfuric acid was poured 20 g of this reaction product, and the resulting mixture was heated and refluxed for 4 hours. After being cooled, the mixture was poured into 50 ml of water and extracted with (C$_2$H$_5$)$_2$O, and the (C$_2$H$_5$)$_2$O was distilled off, after which the residue was distilled under reduced pressure to obtain 1-bromo-4-pentylbicyclo(2,2,2)-octane.

In another flask, 150 ml of concentrated sulfuric acid and 1.3 g of silver sulfate (Ag$_2$SO$_4$) were mixed and cooled to 5° C., and 5 ml of a solutoin of 3 g of the aforesaid 1-bromo-4-pentylbicyclo(2,2,2)octane in n—C$_6$H$_{14}$ was added. Subsequently, 1 ml of 98% HCOOH was gradually added thereto. After the evolution of gas ceased, the reaction solution was added to 600 ml of ice water to deposit crystals. The crystals were collected by filtration to obtain 4-pentylbicyclo[2,2,2]octanecarboxylic acid.

To 30 ml of SOCl$_2$ was added 3.0 g of this reaction product, and the resulting mixture was stirred continuously for 8 hours while maintaining its temperature at 60° C. The mixture was then distilled to obtain 4-pentylbicyclo[2,2,2]octanecarbonyl chloride

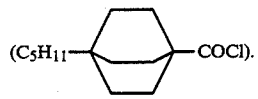

In further another flask, 33 g of

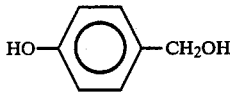

and 900 ml of benzene were mixed, and hydrogen bromide gas (HBr) was blown through the reaction solution for 2 hours under ice-cooling. Thereafter, the solution was stirred continuously for 2 hours and then distilled to obtain p-(α-bromomethyl)phenol

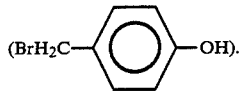

The boiling point of this compound was 125°–126° C./15 mm Hg.

In still another flask, 5 g of Na was dissolved in 300 ml of C$_3$H$_7$OH and the resulting solution was refluxed while adding thereto dropwise 25 g of

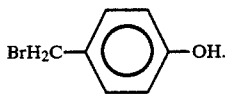

After 4 hours, the reaction mixture was poured into ice water, and the separated oil layer was extracted with (C$_2$H$_5$O)$_2$O. The extract was dehydrated to obtain p-(α-propoxymethyl)phenol

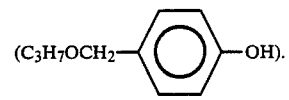

Next, 3 g of pyridine was mixed with 16 g of a solution (content 18%) of the

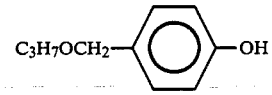

in (C$_2$H$_5$)$_2$O, and 2 g of

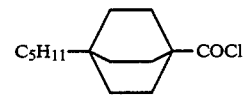

was added dropwise, after which the resulting mixture was refluxed continuously for 3 hours. The reaction mixture was washed with water, and (C$_2$H$_5$)$_2$O was removed, after which the residue was distilled to obtain the objective compound p-(propoxymethyl)phenyl 4-pentylbicyclo[2,2,2]octane carboxylate:

(Sample 64)

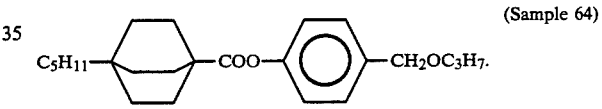

Figure 16:
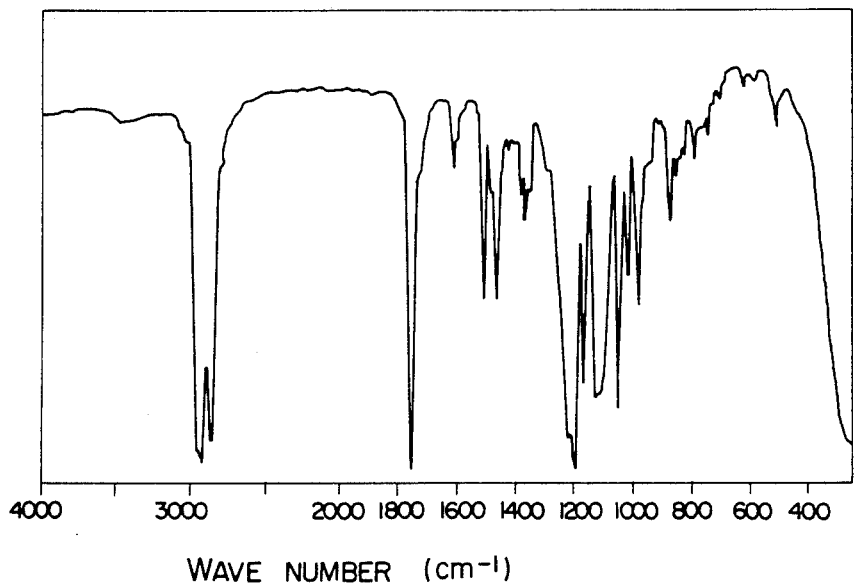

The infrared absorption spectrum of the sample 64 was as shown in FIG. 16, and an absorption band of the ester linkage appeared at 1750 cm$^{-1}$ and that of the ether linkage at 1100 cm$^{-1}$. In the mass spectrum of the sample 64, a peak of ion of the molecule appeared at a m/e ratio of 372. The values of elementary analysis (C 77.41%, H 9.71%) of the sample 64 were in good agreement with the values calculated from the molecular weight (C 77.38%, H 9.74%) for C$_{24}$H$_{37}$O$_3$. From the relation between these facts and the starting compounds, the sample 64 was identified as the liquid crystalline compound of the above formula.

Liquid crystalline compounds corresponding to the above general formula can be produced by the production process according to that of the sample 64. That is to say, R$^4$—CH$_2$COCH$_3$ and CH$_2$=CHCN are first condensed together under basic conditions to obtain

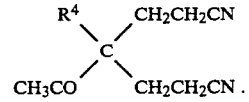

Subsequently, the cyano group is hydrolyzed with an alkali into a carboxyl group, and the thus treated condensation product is heated in (CH$_3$CO)$_2$O to obtain a cyclohexanone derivative

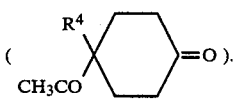

Thereafter, the derivative is heated in the presence of an alkali to obtain a bicyclooctanol derivative

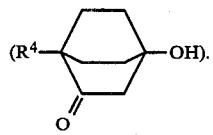

Subsequently, this derivative is subjected to reduction by $NH_2-NH_2$, brominatioin with 48% HBr aqueous solution, acidification treatment with formic acid and treatment with $SOCl_2$ in that order to obtain

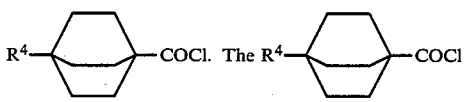

is reacted with the other starting compound

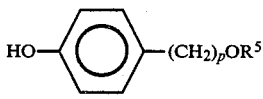

in a basic solution, whereby the objective compound can be obtained.

For example, a liquid crystalline compound of the above general formula in which p=3 can be obtained by esterification reaction of

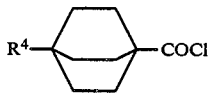

obtained in the same manner as above, with

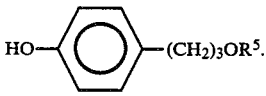

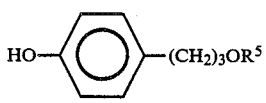

can be obtained, for example, in the following manner. In 600 ml of $CH_3OH$ was dissolved 20 g of Na, and 120 g of 3-bromopropylbenzene

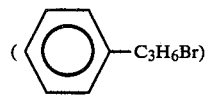

was added dropwise with heating under reflux. After 6 hours, the reaction solution was poured into ice water, and the separated oil layer was extracted with benzene, after which the benzene was distilled off, and the residue was distilled to obtain

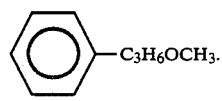

This compound had a boiling point of 96°–98° C./15 mmHg. Next, 195 g of $AlCl_3$ and 100 g of the

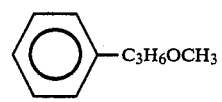

were added to 1.5 liters of $CH_2Cl_2$, and the resulting mixture was cooled with ice under stirring. Subsequently, 79 g of $CH_3COCl$ was gradually added thereto dropwise, and the thus obtained solution was stirred under ice-cooling continuously for 6 hours. This reaction solution was poured into dilute hydrochloric acid, and the $CH_2Cl_2$ layer was separated, after which the $CH_2Cl_2$ was distilled off, and the residue was distilled to obtain

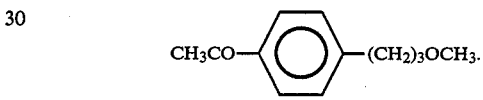

The boiling point of this compound was 94°–95° C./0.3 mm Hg. Sixty-seven grams of this compound and 620 ml of 88% HCOOH were mixed and stirred, after which 310 ml of $(CH_3CO)_2O$, 4 ml of concentrated sulfuric acid and 110 ml of a 35% aqueous hydrogen peroxide solution were added thereto. The resulting solution was heated to 40° to 50° C. and stirred for 8 hours, after which the reaction solution was poured into water, and the separated oil layer was extracted. The solvent was distilled off from the extract, and 100 ml of $CH_3OH$ and 250 ml of a 2N aqueous NaOH solution were added to the residue, after which the resulting solution was heated and refluxed for 2 hours. After being cooled, the reaction solution was made acid with hydrochloric acid, and the oil layer was extracted with benzene. The benzene was distilled off from the extract, and the residue was further distilled to obtain p-(3-methoxypropyl)phenol

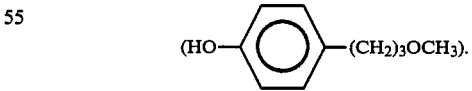

The boiling point of this compound was 106°–108° C./0.3 mm Hg.

Esterification reaction was effected by use of the

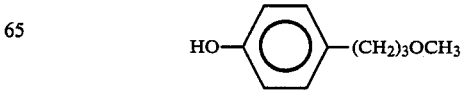

as one starting compound and the already described

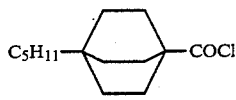

as the other starting compound to obtain the objective compound p-(3-methoxypropyl)phenol-4-pentyl-bicycl(2,2,2)octanecarboxylate:

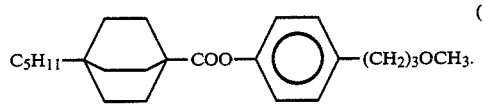
(Sample 65)

Figure 17:
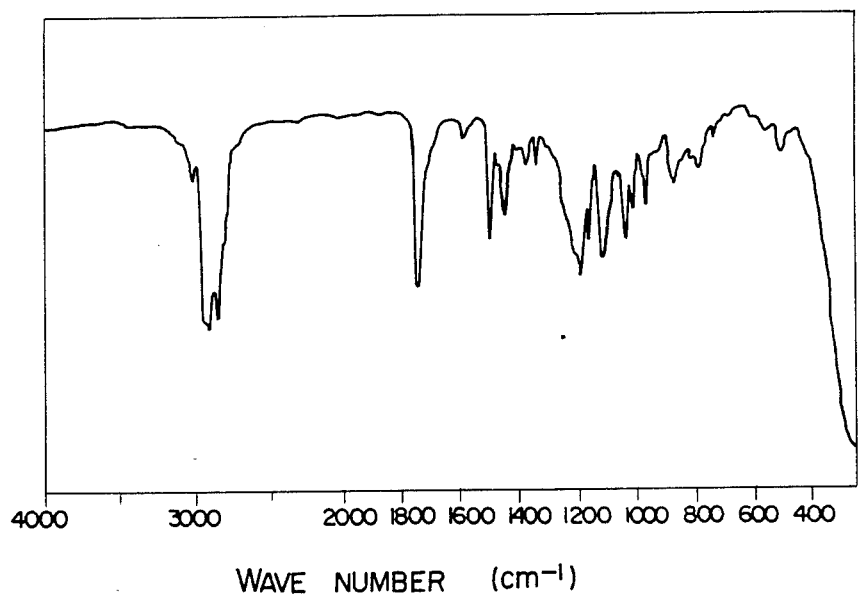

The infrared absorption spectrum of the sample 65 was as shown in FIG. 17, and an absorption band of the ester linkage appeared at 1750 cm$^{-1}$ and that of the ether linkage at 1100 cm$^{-1}$. In the mass spectrum of the sample 65, a peak of ion of the molecule appeared at a m/e ratio of 372. The values of elementary analysis (C 77.32%, H 9.76%) of the sample 65 were in good agreement with the values calculated from the molecular weight (C 77.38%, H 9.74%) for $C_{24}H_{47}O_2$. From the relation between these facts and the starting compounds, it was confirmed that the sample 65 had the above formula.

There are shown in Table 5 the phase transition temperatures of the samples 64 and 65 and other liquid crystalline compounds produced by a production process according to those of the samples 64 and 65.

TABLE 5

| Sample | $R^4$ | $R^5$ | P | C-I | C-N |
|---|---|---|---|---|---|
| 64 | $C_5H_{11}$ | $C_3H_7$ | 1 | 24.0 | (21.0) |
| 65 | $C_5H_{11}$ | $CH_3$ | 3 | 53.2 | 43.1 |
| 66 | $C_5H_{11}$ | $CH_3$ | 1 | 62.0 | (56.0) |
| 67 | $C_7H_{15}$ | $CH_3$ | 1 | 58.0 | (55.0) |
| 68 | $C_7H_{15}$ | $C_2H_5$ | 1 | 31.0 | 26.0 |
| 69 | $C_6H_{13}$ | $CH_3$ | 5 | 59.0 | 37.0 |

EXAMPLE 21

(Characteristics of liquid crystalline compounds incorporated with any of the colorless liquid crystalline compounds produced in the above-mentioned examples)

Nematic liquid crystal compositions having the respective compositions shown in Table 6 were used as base liquid crystal, and each of the samples produced in the above-mentioned examples was incorporated into said compounds. The viscosities, mesomorphic ranges (hereinafter referred to as MR) and Δn of the thus prepared liquid crystal compositions are shown together with those of comparative examples in Tables 8, 9 and 10. Incorporated samples used for compositions are shown in Table 7. Table 10 shows the values of Δn which were measured for compositions obtained by using the sample 59 as an incorporated sample.

The liquid crystal compositions were prepared by adding predetermined amounts of individual colorless liquid crystalline compounds to the base liquid crystals, heating the resulting mixture at 80° to 85° C. for about 1 hour, and then sufficiently stirring and mixing it. The viscosity was measured by using a rotation viscometer. The measurement temperature was 20° C. MR was measured by sealing up each of the prepared liquid crystal compositions in a glass capillary having a diameter of 1 mm, and then observing phase transition with the naked eye.

TABLE 6

| | | |
|---|---|---|
| A | $C_5H_{11}$—⌬—⌬—CN | 50% by weight |
| | $C_7H_{15}$—⌬—⌬—CN | 30% by weight |
| | $C_8H_{17}$—⌬—⌬—CN | 20% by weight |
| B | $C_3H_7$—⟨H⟩—⌬—CN | 34% by weight |
| | $C_5H_{11}$—⟨H⟩—⌬—CN | 34% by weight |
| | $C_7H_{15}$—⟨H⟩—⌬—CN | 20% by weight |
| | $C_6H_{11}$—⟨H⟩—⌬—⌬—CN | 12% by weight |
| C | $C_3H_7$—⟨H⟩—COO—⌬—$OC_5H_{11}$ | 40% by weight |
| | $C_5H_{11}$—⟨H⟩—COO—⌬—$OC_2H_5$ | 20% by weight |
| | $C_5H_{11}$—⟨H⟩—COO—⌬—$OC_5H_{11}$ | 40% by weight |
| D | $C_6H_{13}$—⌬—COO—⌬—$C_5H_{11}$ | 35% by weight |
| | $CH_3O$—⌬—COO—⌬—$C_5H_{11}$ | 65% by weight |
| E | $C_3H_7$—⟨H⟩—⌬—$OC_2H_5$ | 50 mol % |
| | $C_3H_7$—⟨H⟩—⌬—$OC_4H_9$ | 50 mol % |
| F | $C_3H_7$—⟨H⟩—⌬—CN | 50 mol % |
| | $C_5H_{11}$—⟨H⟩—⌬—CN | 50 mol % |

TABLE 7

| Sample No. | Liquid crystalline substance |
|---|---|
| 100 | $C_5H_{11}$—⟨H⟩—⌬—$OC_2H_5$ |

TABLE 7-continued

| Sample No. | Liquid crystalline substance |
|---|---|
| 101 | 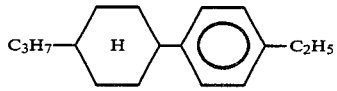 $C_3H_7$—H—⬡—$C_2H_5$ |
| 102 | 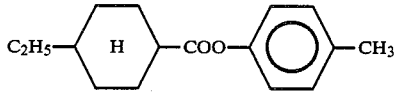 $C_2H_5$—H—COO—⬡—$CH_3$ |
| 103 | 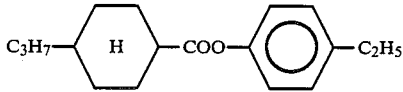 $C_3H_7$—H—COO—⬡—$C_2H_5$ |
| 104 | 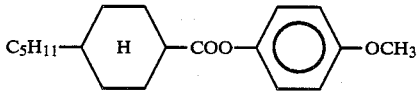 $C_5H_{11}$—H—COO—⬡—$OCH_3$ |
| 105 | 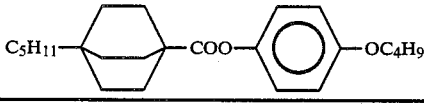 $C_5H_{11}$—⬡—COO—⬡—$OC_4H_9$ |

TABLE 8

| Base liquid crystal | Sample No. | Added amount of sample (wt %) | Viscosity (cp) at 20° C. |
|---|---|---|---|
| A | — | 0 | 55 |
|  | 2 | 5 | 49 |
|  | 5 | 20 | 40 |
|  | 13 | 10 | 45 |
|  | 16 | 15 | 43 |
|  | 18 | 10 | 46 |
|  | 27 | 10 | 50 |
|  | 28 | 10 | 49 |
|  | 29 | 10 | 51 |
|  | 32 | 15 | 44 |
|  | 33 | 15 | 42 |
|  | 57 | 10 | 45 |
|  | 57 | 20 | 39 |
|  | 57 | 30 | 31 |
|  | 58 | 10 | 46 |
|  | 58 | 20 | 40 |
|  | 58 | 30 | 32 |
|  | 59 | 10 | 43 |
|  | 59 | 20 | 37 |
|  | 59 | 30 | 35 |
| B | — | 0 | 29 |
|  | 3 | 20 | 20 |
|  | 4 | 15 | 23 |
|  | 16 | 10 | 26 |
|  | 30 | 15 | 22 |
|  | 34 | 15 | 23 |
|  | 57 | 10 | 25 |
|  | 57 | 15 | 23 |
|  | 57 | 20 | 20 |
|  | 57 | 30 | 19 |
|  | 57 | 40 | 17 |
|  | 58 | 10 | 25 |
|  | 58 | 15 | 23 |
|  | 58 | 20 | 20 |
|  | 58 | 30 | 19 |
|  | 58 | 40 | 17 |
|  | 59 | 10 | 22 |
|  | 59 | 15 | 20 |
|  | 59 | 20 | 18 |
|  | 59 | 30 | 17 |
| C | — | 0 | 29 |
|  | 57 | 10 | 26 |
|  | 57 | 20 | 22 |
|  | 58 | 10 | 26 |
|  | 58 | 20 | 23 |
|  | 59 | 10 | 24 |
|  | 59 | 20 | 20 |
|  | 59 | 30 | 18 |
| D | — | 0 | 58 |
|  | 57 | 10 | 50 |
|  | 57 | 20 | 45 |
|  | 58 | 10 | 50 |
|  | 58 | 20 | 46 |

TABLE 9

| Sample No. | Added amount of sample (wt %) | Viscosity (cp) at 20° C. | MR (°C.) |
|---|---|---|---|
| (Base liquid crystal; A) | | | |
| — | 0 | 55 | *to 60 |
| 102 | 10 | 50 | 2–63 |
| 103 | 10 | 51 | 4–66 |
| 46 | 5 | 43 | −9–64 |
| 47 | 10 | 42 | −11–67 |
| 49 | 10 | 42 | −10–69 |
| 50 | 10 | 40 | −9–68 |
| 52 | 10 | 43 | −12–69 |
| 56 | 10 | 44 | −10–68 |
| 60 | 10 | 56 | *to 69 |
| 60 | 20 | 56 | *to 82 |
| 60 | 30 | 57 | *to 106 |
| 61 | 10 | 56 | *to 72 |
| 61 | 20 | 57 | *to 88 |
| 61 | 30 | 59 | *to 113 |
| 62 | 10 | 56 | *to 68 |
| 62 | 20 | 58 | *to 89 |
| 62 | 30 | 59 | *to 119 |
| 63 | 10 | 56 | *to 70 |
| 63 | 20 | 58 | *to 81 |
| 63 | 30 | 59 | *to 92 |
| (Base liquid crystal; B) | | | |
| — | 0 | 29 | −2–71 |
| 100 | 10 | 28 | −7–67 |
| 100 | 20 | 26 | −10–64 |
| 101 | 10 | 24 | −15–50 |
| 102 | 10 | 27 | −1–67 |
| 103 | 10 | 28 | 0–69.5 |
| 104 | 10 | 27 | −0.5–74 |
| 104 | 30 | Not compatible | |
| 105 | 10 | 26.5 | 3–73 |
| 105 | 30 | 23 | 6–83 |
| 2 | 20 | 20 | −21–63 |
| 13 | 15 | 22 | −19–65 |
| 16 | 10 | 26 | −11–66 |
| 16 | 15 | 23 | −15–64 |
| 44 | 10 | 24 | −12–68 |
| 45 | 10 | 23 | −9–67 |
| 46 | 10 | 25 | −13–69 |
| 47 | 10 | 26 | −13–68 |
| 48 | 10 | 25 | −11–69 |
| 49 | 10 | 24 | −12–68 |
| 50 | 10 | 23 | −10–67 |
| 52 | 10 | 24 | −9–67 |
| 54 | 10 | 24 | −10–69 |
| 56 | 5 | 24 | −13–68 |
| 60 | 10 | 31 | *to 84 |
| 60 | 20 | 32 | *to 93 |
| 60 | 30 | 33 | *to 109 |
| 61 | 10 | 32 | *to 88 |
| 61 | 20 | 32 | *to 109 |
| 61 | 30 | 33 | *to 116 |
| 62 | 10 | 31 | *to 91 |
| 62 | 20 | 32 | *to 103 |
| 62 | 30 | 33 | *to 121 |
| 63 | 10 | 31 | *to 80 |
| 63 | 20 | 32 | *to 92 |
| 63 | 30 | 33 | *to 103 |
| 64 | 10 | 26 | −3–73 |
| 64 | 20 | 24 | −4–75 |

TABLE 9-continued

| Sample No. | Added amount of sample (wt %) | Viscosity (cp) at 20° C. | MR (°C.) |
|---|---|---|---|
| 64 | 30 | 22 | −6−80 |
| 65 | 10 | 26 | −3.5−73 |
| 65 | 30 | 23 | −6.5−78 |
| 69 | 10 | 26.5 | −3.5−74 |
| 69 | 30 | 23.5 | −7−79 |
| (Base liquid crystal; E) | | | |
| — | 0 | 12 | 20−33.5 |
| 64 | 10 | 11.5 | 16−35 |
| 64 | 20 | 10.5 | 14.5−37 |
| 64 | 30 | 9.5 | 12−38 |
| 65 | 10 | 11.5 | 17−35.5 |
| 65 | 30 | 10 | 11−38 |
| 69 | 10 | 11.5 | 16−36 |
| 69 | 30 | 10 | 12−38 |
| (Base liquid crystal; F) | | | |
| — | 0 | 22 | 9−50 |
| 104 | 10 | 21 | 7−53 |
| 104 | 30 | 19 | 13.5−63 |
| 105 | 10 | 21 | 8−51 |
| 105 | 30 | 18.5 | 14−67 |
| 64 | 10 | 20.5 | 7−51 |
| 64 | 20 | 19.5 | 6−52 |
| 64 | 30 | 18 | 5−56 |
| 65 | 10 | 21 | 7−52 |
| 65 | 30 | 18 | 6−58 |
| 69 | 10 | 21 | 8−53 |
| 69 | 30 | 18 | 6−56 |

(*Not crystallized after −40° C./100 hr.)

TABLE 10

| Base liquid crystal | Added amount (wt %) | | | |
|---|---|---|---|---|
| | 0 | 10 | 20 | 30 |
| A | 0.203 | 0.180 | 0.153 | 0.142 |
| B | 0.136 | 0.121 | 0.109 | 0.101 |
| C | 0.081 | 0.074 | 0.071 | 0.063 |

The data shown in the above tables mean as follows.

(1) Each of the liquid crystal compositions incorporated with each of the colorless liquid crystalline compounds of Examples 1 to 10 and Example 14 has a viscosity lower than that of the corresponding base liquid crystal by 10 to 30%.

(2) Each of the liquid crystal compositions incorporated with each of the colorless liquid crystalline compounds of Examples 15 and 16 has a viscosity lower than that of the corresponding base liquid crystal by 15 to 35%.

(3) Each of the liquid crystal compositions incorporated with the colorless liquid crystalline compound of Example 17 has a viscosizy lower than that of the corresponding base liquid crystal by 36 to 41% and has a Δn smaller than that of the latter by 23 to 30% as shown in Table 10.

(4) Each of the liquid crystal compositions incorporated with each of the colorless liquid crystalline compounds of Examples 18 and 19 is increased in viscosity by only 4 cp as compared with the corresponding base liquid crystal, and the upper limit of MR is elevated by 39° to 59° C. in the case of the compound of Example 18 and by 10° to 32° C. in the case of the compound of Example 19.

EXAMPLE 22

(Response properties of liquid crystal display elements using a liquid crystal composition containing any of the colorless liquid crystalline compounds of this invention prepared in Example 21)

TN type liquid crystal display elements were produced by using, as a liquid crystal layer, any of the liquid crystal compositions prepared in Example 21. In these liquid crystal display elements, transparent SnO₂ or InO₃ NESA electrodes were formed on the insides of each of the upper and lower glass substrates, and each orientation controlling film made from an imide polymer was formed thereon in order to orient the liquid crystal molecules. The gap between the upper and lower substrates was controlled so that the thickness of the liquid crystal layer becomes about 10 μm. A voltage of 6 V was applied to each of the liquid crystal display elements at ambient temperature (30° C.), and the response time was measured. The results are shown in Table 11.

TABLE 11

| Base liquid crystal | Sample No. | Added amount of sample (wt %) | Response time (sec) |
|---|---|---|---|
| B | — | 0 | 3.6 |
| | 5 | 20 | 1.7 |
| | 57 | 20 | 1.8 |
| | 58 | 20 | 1.8 |
| | 59 | 20 | 1.4 |
| C | — | 0 | 3.4 |
| | 69 | 30 | 1.2 |

As explained above, when any of the colorless liquid crystalline compounds of this invention is used, it becomes possible to obtain a colorless liquid crystalline composition having a wide mesomorphic range from the circumstance of low temperatures to that of high temperatures, of course, including room temperature. In addition, said compounds have an effect of imparting excellent response properties to a liquid crystal display element using the colorless liquid crystal composition.

What is claimed is:

1. A colorless liquid crystalline compound of the formula:

or

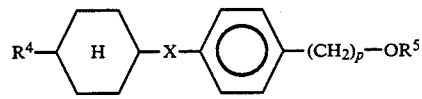

wherein R⁴ and R⁵ are independently a straight-chain or branched-chain alkyl group having 12 or less carbon atoms; X is —COO— or —OCO—; and p is an integer of 1 to 8.

2. A colorless liquid crystalline compound of the formula

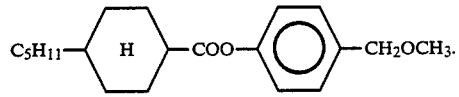

3. A colorless liquid crystalline compound of the formula

4. A colorless liquid crystalline compound of the formula
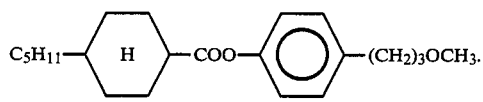
wherein n is an integer of 1 to 8, and m is an integer from 1 to 12.